US011801391B2

United States Patent
Chin et al.

(10) Patent No.: US 11,801,391 B2
(45) Date of Patent: Oct. 31, 2023

(54) MITIGATING FALSE MESSAGES AND EFFECTS THEREOF IN MULTI-CHAMBER LEADLESS PACEMAKER SYSTEMS AND OTHER IMD SYSTEMS

(71) Applicant: Pacesetter, Inc., Sylmar, CA (US)

(72) Inventors: Donald Chin, Palo Alto, CA (US); Matthew G. Fishler, Scotts Valley, CA (US); Benjamin T. Persson, Saratoga, CA (US); Suresh Gurunathan, Palo Alto, CA (US)

(73) Assignee: Pacesetter, Inc., Sylmar, CA (US)

( * ) Notice: Subject to any disclaimer, the term of this patent is extended or adjusted under 35 U.S.C. 154(b) by 489 days.

(21) Appl. No.: 17/022,994

(22) Filed: Sep. 16, 2020

(65) Prior Publication Data

US 2021/0093873 A1 Apr. 1, 2021

Related U.S. Application Data

(60) Provisional application No. 62/907,396, filed on Sep. 27, 2019.

(51) Int. Cl.
*A61N 1/372* (2006.01)
*A61N 1/368* (2006.01)
*G16H 40/67* (2018.01)
*A61N 1/375* (2006.01)
(Continued)

(52) U.S. Cl.
CPC ......... *A61N 1/37254* (2017.08); *A61N 1/368* (2013.01); *A61N 1/3684* (2013.01); *A61N 1/37* (2013.01); *A61N 1/3756* (2013.01); *A61N 1/37217* (2013.01); *A61N 1/37512* (2017.08); *A61N 1/39622* (2017.08); *G16H 40/67* (2018.01)

(58) Field of Classification Search
CPC .. A61N 1/37254; A61N 1/368; A61N 1/3684; A61N 1/37; A61N 1/37217; A61N 1/37512; A61N 1/3756; A61N 1/39622; A61N 1/3706; A61N 1/37288; A61N 1/3682
See application file for complete search history.

(56) References Cited

U.S. PATENT DOCUMENTS

| | | |
|---|---|---|
| 6,427,088 B1 | 7/2002 | Bowman |
| 6,443,891 B1 | 9/2002 | Grevious |
| 6,535,766 B1 | 3/2003 | Thompson et al. |

(Continued)

OTHER PUBLICATIONS

Response to Office Action dated Dec. 8, 2022, U.S. Appl. No. 17/022,774, filed Sep. 16, 2020.

(Continued)

*Primary Examiner* — Mallika D Fairchild
(74) *Attorney, Agent, or Firm* — Vierra Magen Marcus LLP

(57) ABSTRACT

Implantable medical devices (IMDs) described herein, and methods for use therewith described herein, reduce how often an IMD accepts a false message and/or reduce adverse effects of an IMD accepting a false message. Such IMDs can be leadless pacemakers (LPs), or implantable cardio defibrillators (ICDs), but are not limited thereto. Such embodiments can be used help multiple IMDs (e.g., multiple LPs) implanted within a same patient maintain synchronous operation, such as synchronous multi-chamber pacing.

10 Claims, 9 Drawing Sheets

(51) Int. Cl.
*A61N 1/37* (2006.01)
*A61N 1/39* (2006.01)

(56) References Cited

U.S. PATENT DOCUMENTS

| | | | |
|---|---|---|---|
| 7,218,969 B2 | 5/2007 | Yallapureddy | |
| 8,509,911 B2 | 8/2013 | Li | |
| 8,512,220 B2 | 8/2013 | Lovett et al. | |
| 8,607,305 B2 | 12/2013 | Neystadt | |
| 9,168,380 B1 | 10/2015 | Greenhut et al. | |
| 10,052,491 B1 | 8/2018 | Chin | |
| 10,173,068 B2 | 1/2019 | Chin et al. | |
| 10,722,722 B2 | 7/2020 | Chin et al. | |
| 2002/0045920 A1 | 4/2002 | Thompson | |
| 2003/0034911 A1* | 2/2003 | Martini | H04L 1/0061 341/173 |
| 2005/0283198 A1 | 12/2005 | Haubrich | |
| 2008/0027501 A1 | 1/2008 | Haubrich et al. | |
| 2011/0082379 A1 | 4/2011 | Sullivan | |
| 2015/0147073 A1 | 5/2015 | Nonaka | |
| 2016/0038747 A1 | 2/2016 | Maile | |
| 2016/0067490 A1 | 3/2016 | Carney et al. | |
| 2016/0121127 A1 | 5/2016 | Fishler et al. | |
| 2016/0121128 A1 | 5/2016 | Fishler et al. | |
| 2016/0121129 A1 | 5/2016 | Persson et al. | |
| 2016/0250483 A1 | 9/2016 | Klimovitch et al. | |
| 2016/0310733 A1 | 10/2016 | Sheldon et al. | |
| 2017/0054516 A1 | 2/2017 | Schmidt | |
| 2017/0132120 A1 | 5/2017 | Salameh | |
| 2017/0216610 A1 | 8/2017 | Yoder | |
| 2017/0257761 A1 | 9/2017 | Rodriquez | |
| 2017/0317518 A1 | 11/2017 | Olson | |
| 2018/0176293 A1 | 6/2018 | Ding et al. | |
| 2018/0214703 A1 | 8/2018 | Chin | |
| 2018/0214704 A1 | 8/2018 | Chin | |

OTHER PUBLICATIONS

Communication pursuant to Rules 161(1) and 162 EPC dated May 6, 2022, European Patent Application No. 20786395.2-1122.
U.S. Appl. No. 17/022,774, filed Sep. 16, 2020.
International Preliminary Report on Patentability dated Apr. 7, 2022, International Application No. PCT/US2020/052003.
Response to Office Action dated Jun. 3, 2022, U.S. Appl. No. 17/022,774, filed Sep. 16, 2020.
Notice of Allowance dated Feb. 3, 2023, U.S. Appl. No. 17/022,774, filed Sep. 16, 2020.
Non-final Office Action dated Mar. 11, 2022, U.S. Appl. No. 17/022,774, filed Sep. 16, 2020.
Response to Office Action dated Jun. 8, 2022, European Patent Application No. 20786395.2.
Final Office Action dated Sep. 21, 2022, U.S. Appl. No. 17/022,774, filed Sep. 16, 2020.
Invitation to Pay Additional Fees dated Dec. 8, 2020, International Application No. PCT/US2020/052003.

* cited by examiner

MITIGATING FALSE MESSAGES AND EFFECTS THEREOF IN MULTI-CHAMBER LEADLESS PACEMAKER SYSTEMS AND OTHER IMD SYSTEMS

PRIORITY CLAIM

This application claims priority to U.S. Provisional Patent Application No. 62/907,396, filed Sep. 27, 2019, which is incorporated herein by reference in its entirety.

RELATED APPLICATION

This application is related to commonly assigned U.S. patent application Ser. No. 17/022,774, titled MITIGATING FALSE MESSAGES AND EFFECTS THEREOF IN MULTI-CHAMBER LEADLESS PACEMAKER SYSTEMS AND OTHER IMD SYSTEMS filed the same date as the present application, which is incorporated herein by reference in its entirety.

FIELD OF TECHNOLOGY

Embodiments described herein generally relate to methods and systems for providing and improving communication between implantable medical devices, one or more of which may be a leadless cardiac pacemaker.

BACKGROUND

Implantable medical devices and systems often rely on proper communication to operate correctly. For example, in a dual chamber leadless pacemaker system, implant-to-implant (i2i) communication is critical for proper synchronization and operation of the system. However, noise may cause one or more devices of such a system to falsely detect an i2i message and inappropriately respond thereto. For a more specific example, noise may cause a ventricular leadless pacemaker (LP) to falsely detect a message from an atrial LP, which then could trigger the ventricular LP to pace at an inappropriate high-rate, and more generally, at inappropriate times. For another example, an atrial LP can falsely detect a message that causes the atrial LP to pace the right atrium at a rate that is much higher than a rate at which a ventricular LP is pacing the right ventricle, thereby resulting in unsynchronized pacing. To reduce the probability of an implantable medical device falsely detecting i2i messages, such i2i messages may include redundant data for error detection and correction. However, due to the desire to keep the power consumption low, the i2i messaging and/or error correction and detection scheme may be simple and false messages may still get through.

SUMMARY

Certain embodiments of the present technology are related to methods for use by a leadless pacemaker (LP) implanted in or on a first cardiac chamber of a patient also having an implantable medical device (IMD) remotely located relative to the LP, wherein the LP is configured to pace the first cardiac chamber and adjust a pacing rate at which the first cardiac chamber is paced based on a pacing rate indicator included in an implant-to-implant (i2i) message received from the IMD. In accordance with certain embodiments, the method includes the LP monitoring for i2i messages, and in response to the LP receiving an i2i message including a pacing rate indicator that would cause an adjustment to the pacing rate exceeding a rate adjustment threshold, the LP limiting the adjustment to the pacing rate to a specified amount. In accordance with certain embodiments, the specified amount, by which the LP limits an adjustment to the pacing rate in response to receiving an i2i message including a pacing rate indicator that would cause an adjustment to the pacing rate exceeding a rate adjustment threshold, comprises the rate adjustment threshold. In accordance with certain embodiments, the specified amount, by which the LP limits an adjustment to the pacing rate in response to receiving an i2i message including a pacing rate indicator that would cause an adjustment to the pacing rate exceeding a rate adjustment threshold, comprises a predetermined value or a predetermined function of a present pacing rate. In accordance with certain embodiments, the LP comprises a first LP (LP1), and the IMD comprises a second LP (LP2) implanted in or on a second cardiac chamber. For example, the first cardiac chamber comprises a right atrial (RA) chamber and the second cardiac chamber comprises a right ventricular (RV) chamber. In accordance with certain embodiments, the LP is implanted in or on the RV chamber, and the IMD comprises a subcutaneous implantable cardioverter defibrillator (S-ICD). In certain such embodiments, the i2i messages are transmitted and received via conductive communication.

Certain embodiments of the present technology are related to an implantable LP configured to be implanted in or on a first cardiac chamber of a patient and configured to pace the first cardiac chamber and adjust a pacing rate at which the first cardiac chamber is paced based on a pacing rate indicator included in an i2i message received from an IMD remotely located relative to the LP. Such an LP can include at least one receiver configured to receive i2i messages, and a controller configured to limit an adjustment to the pacing rate to a specified amount, in response to the LP receiving an i2i message including a pacing rate indicator that would cause an adjustment to the pacing rate to exceed a rate adjustment threshold. In accordance with certain embodiments, the specified amount, by which the controller limits an adjustment to the pacing rate in response to receiving an i2i message including a pacing rate indicator that would cause an adjustment to the pacing rate exceeding a rate adjustment threshold, comprises the rate adjustment threshold. In accordance with certain embodiments, the specified amount, by which the controller limits an adjustment to the pacing rate in response to receiving an i2i message including a pacing rate indicator that would cause an adjustment to the pacing rate exceeding a rate adjustment threshold, comprises a predetermined value or a predetermined function of a present pacing rate. In accordance with certain embodiments, the LP comprises a first LP (LP1), and the IMD comprises a second LP (LP2) implanted in or on a second cardiac chamber. For example, the first cardiac chamber comprises an RA chamber and the second cardiac chamber comprises an RV chamber. In accordance with certain embodiments, the LP is implanted in or on the RV chamber, and the IMD comprises an S-ICD. In certain such embodiments, the i2i messages are transmitted and received via conductive communication.

In accordance with certain embodiments where an LP monitors for i2i messages, the LP expects to receive an i2i message within an expected period from an IMD remotely located relative to the LP. In response to the LP not receiving an i2i message within the expected period, the LP reduces the pacing rate at which the LP paces the first cardiac chamber. In accordance with certain embodiments, the expected period comprises a predetermined period of time, or a predetermined number (N) of cardiac cycles, where N is an integer that is equal to or greater than 1. In accordance with certain embodiments, an amount by which the LP reduces the pacing rate at which the LP paces the first cardiac chamber, in response to the LP not receiving an i2i message within the expected period, comprises a predetermined value, or a predetermined function of a present pacing rate. In certain such embodiments, the LP limits how much the pacing rate is reduced, in response to the LP not receiving an i2i message within the expected period, such that the pacing rate will not fall below a predetermined minimum rate. In accordance with certain embodiments, the LP comprises a first LP (LP1), the IMD comprises a second LP (LP2) implanted in or on a second cardiac chamber, the first cardiac chamber comprises an RA chamber, and the second cardiac chamber comprises an RV chamber. In accordance with certain embodiments, the i2i messages are transmitted and received via conductive communication, the LP is implanted in or on the RV chamber, and the IMD comprises an S-ICD. In certain such embodiments, the i2i messages are transmitted and received via conductive communication.

In accordance with certain embodiments, an LP comprises at least one receiver configured to receive i2i messages, and a controller configured to reduce the pacing rate at which the LP paces the first cardiac chamber, in response to the LP not receiving an i2i message within an expected period. In accordance with certain embodiments, the expected period comprises a predetermined period of time, or a predetermined number (N) of cardiac cycles, where N is an integer that is equal to or greater than 1. In accordance with certain embodiments, an amount by which the controller reduces the pacing rate at which the LP paces the first cardiac chamber, in response to the LP not receiving an i2i message within an expected period, comprises a predetermined value, or a predetermined function of a present pacing rate. In certain such embodiments, the controller limits how much the pacing rate is reduced, in response to the LP not receiving an i2i message within an expected period, such that the pacing rate will not fall below a predetermined minimum rate.

Certain embodiments of the present technology are related to a method involving an LP monitoring for i2i messages, and in response to the LP receiving at least a specified plurality of i2i messages that include a same pacing rate indicator, the LP adjusting the pacing rate at which the first cardiac chamber is paced based on the pacing rate indicator included in the specified plurality of i2i messages received by the LP. The method also includes in response to the LP not receiving at least the specified plurality of i2i messages that include a same pacing rate indicator, the LP not adjusting the pacing rate at which the first cardiac chamber is paced based on a pacing rate indicator included in an i2i message received by the LP. In accordance with certain embodiments, the specified plurality of i2i messages comprise at least N consecutive i2i messages that include the same pacing rate indicator, where N is a predetermined integer that is equal to or greater than 2, and the IMD is configured to send at least N consecutive i2i messages including a same pacing rate indicator to the LP whenever the IMD changes the rate at which the LP paces the first cardiac chamber. In accordance with other embodiments, the specified plurality of i2i messages comprise at least M out of N i2i messages that include the same pacing rate indicator, where M is a predetermined integer that is equal to or greater than 2, and where N is a predetermined integer that is greater than M, and the IMD is configured to send at least N i2i messages including a same pacing rate indicator to the LP whenever the IMD changes the rate at which the LP paces the first cardiac chamber. In certain embodiments, the LP comprises a first LP (LP1), and the IMD comprises a second LP (LP2) implanted in or on a second cardiac chamber. For example, the first cardiac chamber comprises an RA chamber, and the second cardiac chamber comprises an RV chamber. In other embodiments, the LP is implanted in or on the RV chamber, and the IMD comprises an S-ICD. In certain such embodiments, the i2i messages are transmitted and received via conductive communication.

Certain embodiments of the present technology are related to a system comprising an LP and an IMD, wherein the LP is configured to be implanted in or on a first cardiac chamber of a patient and configured to pace the first cardiac chamber, and the IMD remotely located relative to the LP. Further, the LP includes a controller configured to adjust a pacing rate at which the first cardiac chamber is paced based on pacing rate indicators included in i2i messages received from the IMD. In response to the LP receiving at least a specified plurality of i2i messages that include a same pacing rate indicator, the controller of the LP is configured to adjust the pacing rate at which the first cardiac chamber is paced based on the pacing rate indicator included in the specified plurality of i2i messages received by the LP. In response to the LP not receiving at least the specified plurality of i2i messages that include a same pacing rate indicator, the controller of the LP is configured to not adjust the pacing rate at which the first cardiac chamber is paced based on a pacing rate indicator included in an i2i message received by the LP. In certain such embodiments, the specified plurality of i2i messages comprise at least N consecutive i2i messages that include the same pacing rate indicator, where N is a predetermined integer that is equal to or greater than 2, and the IMD is configured to send at least N consecutive i2i messages including a same pacing rate indicator to the LP whenever the IMD changes the rate at which the LP is to pace the first cardiac chamber. In accordance with other embodiments, the specified plurality of i2i messages comprise at least M out of N i2i messages that include the same pacing rate indicator, where M is a predetermined integer that is equal to or greater than 2, and where N is a predetermined integer that is greater than M, and the IMD is configured to send at least N i2i messages including a same pacing rate indicator to the LP whenever the IMD changes the rate at which the LP paces the first cardiac chamber. In certain embodiments, the LP comprises a first LP (LP1), and the IMD comprises a second LP (LP2) implanted in or on a second cardiac chamber. For example, the first cardiac chamber comprises an RA chamber, and the second cardiac chamber comprises an RV chamber. In other embodiments, the LP is implanted in or on the RV chamber, and the IMD comprises an S-ICD. In certain such embodiments, the i2i messages are transmitted and received via conductive communication.

In a method according to certain embodiments of the present technology, an IMD transmits i2i messages to the LP, wherein a subset of the i2i messages transmitted by the IMD to the LP include pacing rate indicators. In certain such embodiments, the LP monitors for i2i messages and adjusts the pacing rate at which a first cardiac chamber is paced based on at least some pacing rate indicators included in at least some of the i2i messages received by the LP from the IMD. In certain such embodiments, i2i messages including pacing rate indicators that are transmitted from the IMD to the LP include a longer error detection and correction code compared to an error detection and correction code included at least some of the i2i messages not including pacing rate indicators that are transmitted from the IMD to the LP. In certain such embodiments, the error detection and correction codes comprise cyclic redundancy check (CRC) codes. In certain such embodiments, the LP comprises a first LP (LP1), and the IMD comprises a second LP (LP2) implanted in or on a second cardiac chamber. For example, the first cardiac chamber comprises an RA chamber, and the second cardiac chamber comprises an RV chamber. In other embodiments the LP is implanted in or on the RV chamber and the IMD comprises an S-ICD. In certain such embodiments, the i2i messages are transmitted and received via conductive communication.

In accordance with certain embodiments, a system comprises an LP configured to be implanted in or on a first cardiac chamber of a patient and configured to pace the first cardiac chamber, and an IMD remotely located relative to the LP. The LP is configured to adjust a pacing rate at which the first cardiac chamber is paced based on pacing rate indicators included in i2i messages received from the IMD. In certain such embodiments, the IMD is configured to include a longer error detection and correction code in i2i messages including pacing rate indicators transmitted by the IMD to the LP, compared to an error detection and correction code included in at least some of the i2i messages not including pacing rate indicators that are transmitted from the IMD to the LP. In certain such embodiments, the error detection and correction codes comprise CRC codes. In certain such embodiments, the LP comprises a first LP (LP1), and the IMD comprises a second LP (LP2) implanted in or on a second cardiac chamber. For example, the first cardiac chamber comprises an RA chamber, and the second cardiac chamber comprises an RV chamber. In other embodiments the LP is implanted in or on the RV chamber and the IMD comprises an S-ICD. In certain such embodiments, the i2i messages are transmitted and received via conductive communication.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

Embodiments of the present technology relating to both structure and method of operation may best be understood by referring to the following description and accompanying drawings, in which similar reference characters denote similar elements throughout the several views.

DETAILED DESCRIPTION

Certain embodiments of the present technology related to implantable medical devices (IMDs), and methods for use therewith, that reduce how often false messages are accepted and/or reduce the effects of IMDs receiving false messages. Such embodiments are especially useful with a system that includes one or more leadless cardiac pacemakers, but are not limited to use therewith. Before providing additional details of the specific embodiments of the present technology mentioned above, an exemplary system in which embodiments of the present technology can be used will first be described with reference to FIGS. 1-5. More specifically, FIGS. 1-5 will be used to describe an exemplary cardiac pacing system, wherein pacing and sensing operations can be performed by multiple medical devices, which may include one or more leadless cardiac pacemakers, an ICD, such as a subcutaneous-ICD (S-ICD), and/or a programmer to reliably and safely coordinate pacing and/or sensing operations. A leadless cardiac pacemaker can also be referred to more succinctly herein as a leadless pacemaker (LP). Where a cardiac pacing system includes an S-ICD, the S-ICD may perform certain sensing operations and may communicate with one or more LPs by sending and/or receiving messages to and/or from one or more LPs, as can be appreciated from the below discussion. Where a cardiac pacing system includes a programmer, the programmer may be used to program one or more IMDs, download information to one or more IMDs, and/or upload information from one or more IMDs, as can be appreciated from the below description.

Figure 1:
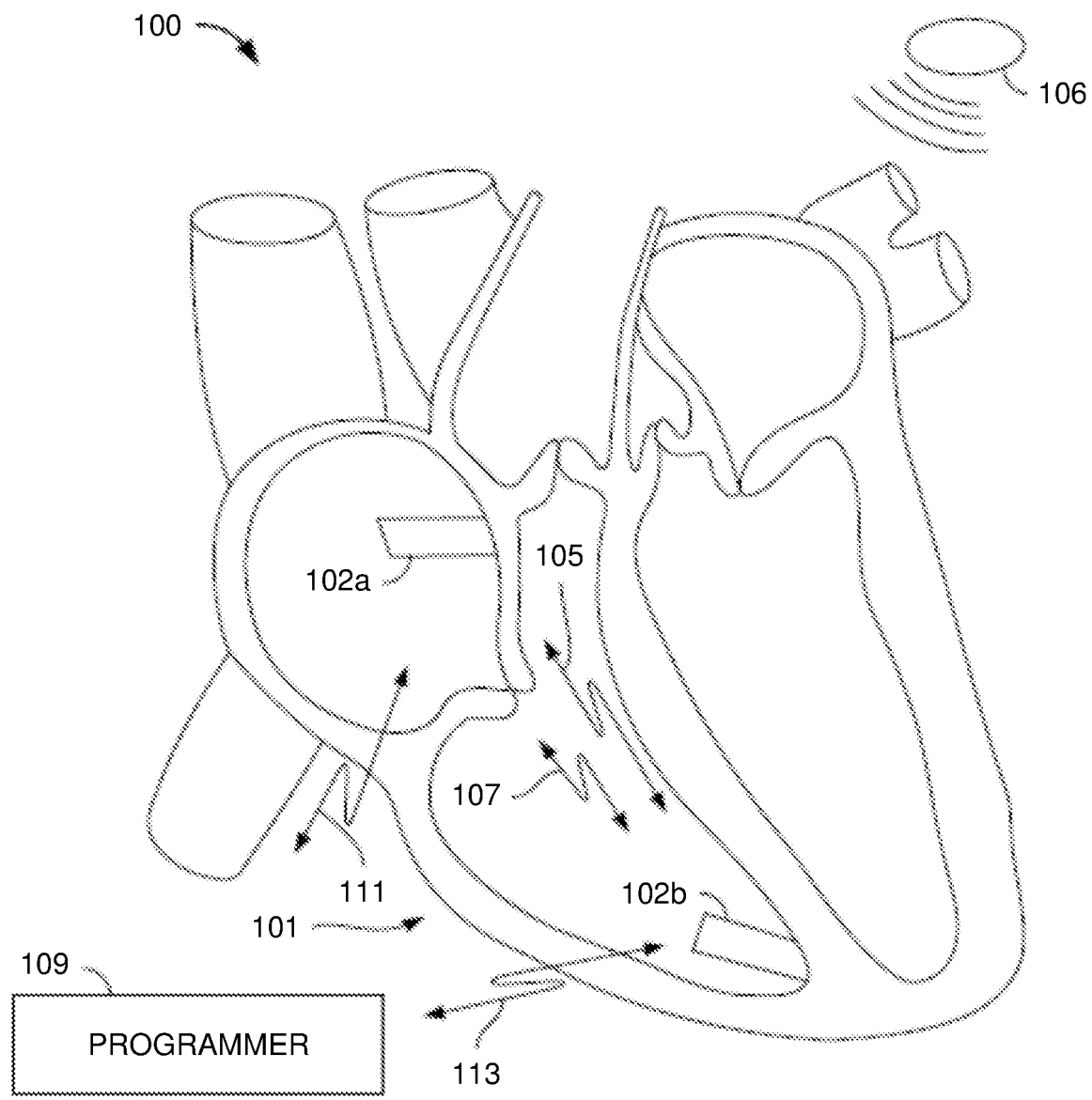
FIG. 1 illustrates a system formed in accordance with certain embodiments herein as implanted in a heart.

FIG. 1 illustrates a system 100 that is configured to be implanted in a heart 101. The system 100 includes two or more leadless pacemakers (LPs) 102a and 102b located in different chambers of the heart. LP 102a is located in a right atrium, while LP 102b is located in a right ventricle. LPs 102a and 102b communicate with one another to inform one another of various local physiologic activities, such as local intrinsic events, local paced events and the like. LPs 102a and 102b may be constructed in a similar manner, but operate differently based upon which chamber LP 102a or 102b is located. The LPs 102a and 102b may sometimes be referred to collectively herein as the LPs 102, or individually as an LP 102.

In certain embodiments, LPs 102a and 102b communicate with one another, and/or with an ICD 106, by conductive communication through the same electrodes that are used for sensing and/or delivery of pacing therapy. The LPs 102a and 102b may also be able to use conductive communication to communicate with an external device, e.g., a programmer 109, having electrodes placed on the skin of a patient within with the LPs 102a and 102b are implanted. While not shown (and not preferred, since it would increase the size and power consumption of the LPs 102a and 102b), the LPs 102a and 102b can potentially include an antenna and/or telemetry coil that would enable them to communicate with one another, the ICD 106 and/or an external device using RF or inductive communication. While only two LPs are shown in FIG. 1, it is possible that more than two LPs can be implanted in a patient. For example, to provide for biventricular pacing and/or cardiac resynchronization therapy (CRT), in addition to having LPs implanted in the right atrial (RA) chamber and the right ventricular (RV) chamber, a further LP can be implanted in the left ventricular (LV) chamber.

In some embodiments, one or more LP 102a can be co-implanted with the ICD 106. Each LP 102a uses two or more electrodes located within, on, or within a few centimeters of the housing of the pacemaker, for pacing and sensing at the cardiac chamber, for bidirectional communication with one another, with the programmer 109, and the ICD 106.

While the methods, devices and systems described herein include examples primarily in the context of LPs, it is understood that the methods, devices and systems described herein may be utilized with various other types of IMDs. By way of example, the methods, devices and systems may dynamically control communication between various IMDs implanted in a human, not just LPs. Certain embodiments enable a first IMD to receive communication messages from at least a second IMD through conductive communication over at least a first channel. It should also be understood that the embodiments described herein can be used for communication between more than two IMDs, and are not limited to communication between just first and second IMDs. The methods, devices and systems may also be used for communication between two or more IMDs implanted within the same chamber that may be the same type of IMD or may be different types of IMDs. The methods, devices and systems may also be used for communication between two or more IMDs in a system including at least one IMD that is not implanted within a cardiac chamber, but rather, is implanted epicardially, transmurally, intravascularly (e.g., coronary sinus), or subcutaneously (e.g., S-ICD), etc.

Figure 2:
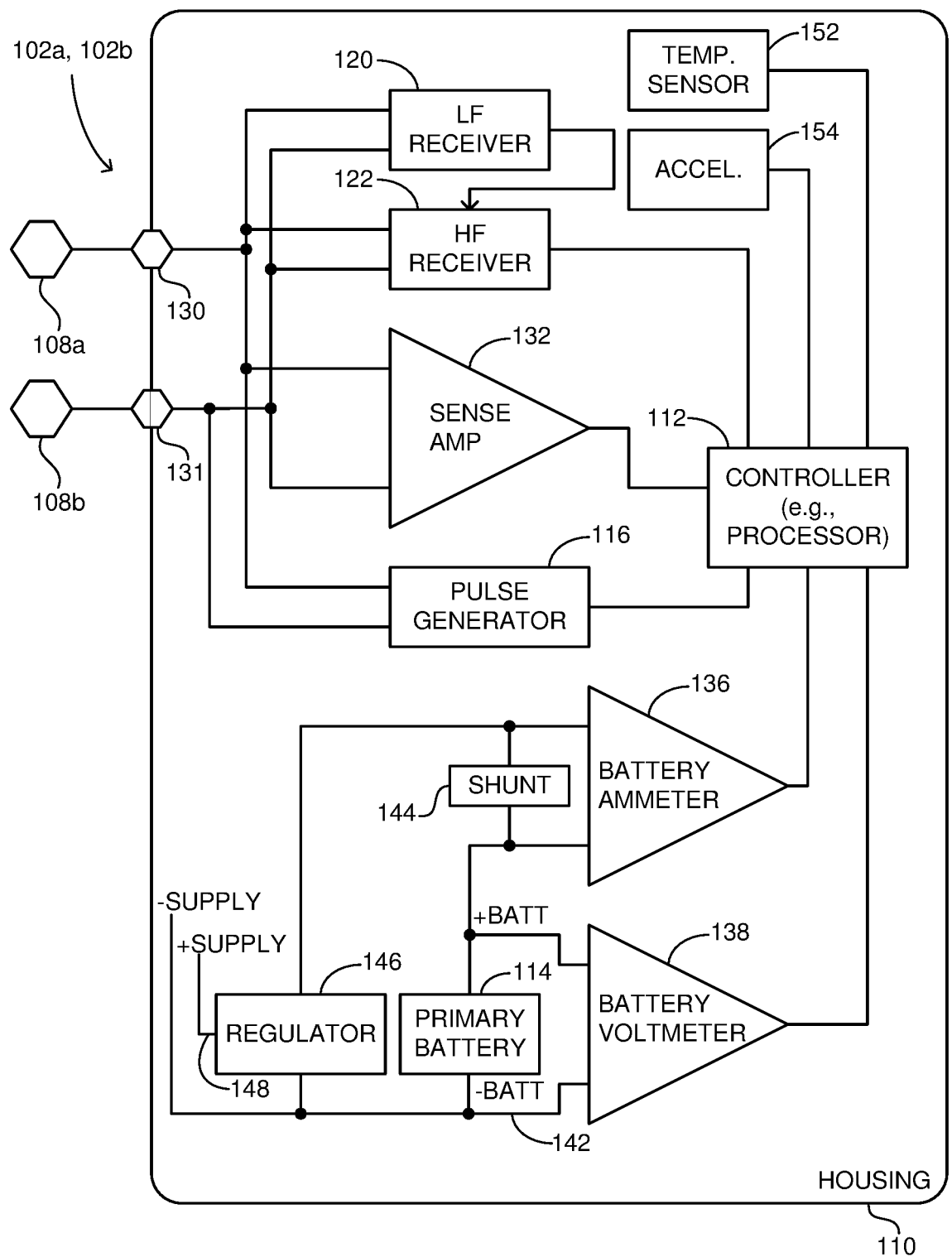
FIG. 2 is a block diagram of a single LP in accordance with certain embodiments herein.
Figure 3:
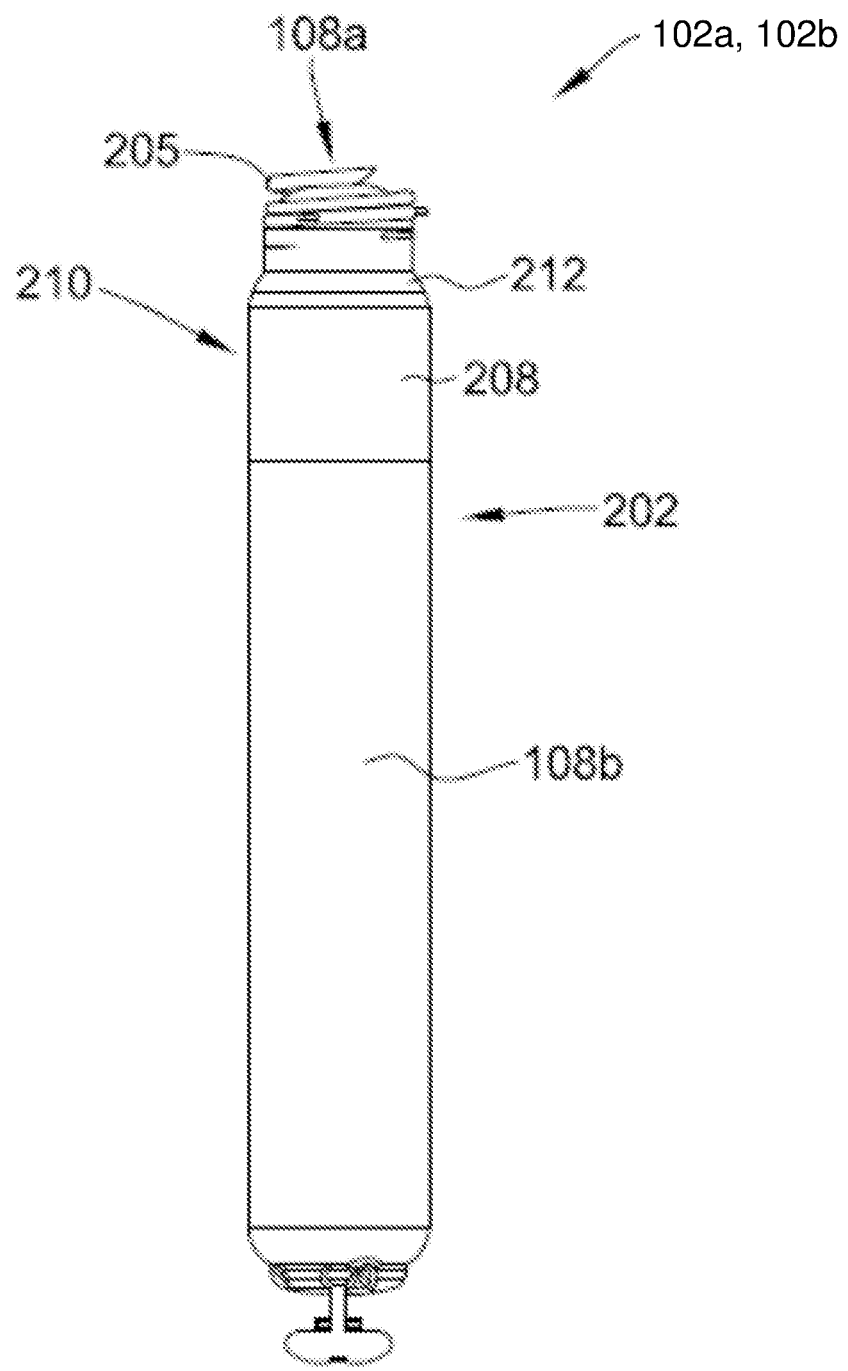
FIG. 3 illustrates an LP in accordance with certain embodiments herein.

Referring to FIG. 2, a block diagram shows an embodiment for portions of the electronics within LPs 102a, 102b configured to provide conductive communication through the sensing/pacing electrode. One or more of LPs 102a and 102b include at least two leadless electrodes configured for delivering cardiac pacing pulses, sensing evoked and/or natural cardiac electrical signals, and uni-directional or bi-directional communication. In FIG. 2 (and FIG. 3) the two electrodes shown therein are labeled 108a and 108b. Such electrodes can be referred to collectively as the electrodes 108, or individually as an electrode 108. An LP 102, or other type of IMD, can include more than two electrodes 108, depending upon implementation.

In FIG. 2, each of the LPs 102a, 102b is shown as including first and second receivers 120 and 122 that collectively define separate first and second communication channels 105 and 107 (FIG. 1), (among other things) between LPs 102a and 102b. Although first and second receivers 120 and 122 are depicted, in other embodiments, each LP 102a, 102b may only include the first receiver 120, or may include additional receivers other than first and second receivers 120 and 122. As will be described in additional detail below, the pulse generator 116 can function as a transmitter that transmits i2i communication signals using the electrodes 108. In certain embodiments, LPs 102a and 102b may communicate over more than just first and second communication channels 105 and 107. In certain embodiments, LPs 102a and 102b may communicate over one common communication channel 105. More specifically, LPs 102a and 102b can communicate conductively over a common physical channel via the same electrodes 108 that are also used to deliver pacing pulses. Usage of the electrodes 108 for communication enables the one or more LPs 102a and 102b to perform antenna-less and telemetry coil-less communication.

The receivers 120 and 122 can also be referred to, respectively, as a low frequency (LF) receiver 120 and a high frequency (HF) receiver 122, because the receiver 120 is configured to monitor for one or more signals within a relatively low frequency range (e.g., below 100 kHz) and the receiver 122 is configured to monitor for one or more signals within a relatively high frequency range (e.g., above 100 kHz). In certain embodiments, the receiver 120 (and more specifically, at least a portion thereof) is always enabled and monitoring for a wakeup notice, which can simply be a wakeup pulse, within a specific low frequency range (e.g., between 1 kHz and 100 kHz); and the receiver 122 is selectively enabled by the receiver 120. The receiver 120 is configured to consume less power than the receiver 122 when both the first and second receivers are enabled. Accordingly, the receiver 120 can also be referred to as a low power receiver 120, and the receiver 122 can also be referred to as a high power receiver 122. The low power receiver 120 is incapable of receiving signals within the relatively high frequency range (e.g., above 100 kHz), but consumes significantly less power than the high power receiver 122. This way the low power receiver 120 is capable of always monitoring for a wakeup notice without significantly depleting the battery (e.g., 114) of the LP. In accordance with certain embodiments, the high power receiver 122 is selectively enabled by the low power receiver 120, in response to the low power receiver 120 receiving a wakeup notice, so that the high power receiver 122 can receive the higher frequency signals, and thereby handle higher data throughput needed for effective i2i communication without unnecessarily and rapidly depleting the battery of the LP (which the high power receiver 122 may do if it were always enabled).

In accordance with certain embodiments, when one of the LPs 102a and 102b senses an intrinsic event or delivers a paced event, the corresponding LP 102a, 102b transmits an implant event message to the other LP 102a, 102b. For example, when an atrial LP 102a senses/paces an atrial event, the atrial LP 102a transmits an implant event message including an event marker indicative of a nature of the event (e.g., intrinsic/sensed atrial event, paced atrial event). When a ventricular LP 102b senses/paces a ventricular event, the ventricular LP 102b transmits an implant event message including an event marker indicative of a nature of the event (e.g., intrinsic/sensed ventricular event, paced ventricular event). In certain embodiments, each LP 102a, 102b transmits an implant event message to the other LP 102a, 102b preceding the actual pace pulse so that the remote LP can blank its sense inputs in anticipation of that remote pace pulse (to prevent inappropriate crosstalk sensing).

The implant event messages may be formatted in various manners. As one example, each event message may include a leading trigger pulse (also referred to as an LP wakeup notice, wakeup pulse or wakeup signal) followed by an event marker. The notice trigger pulse (also referred to as the wakeup notice, wakeup pulse or wakeup signal) is transmitted over a first channel (e.g., with a pulse duration of approximately 10 µs to approximately 1 ms and/or within a fundamental frequency range of approximately 1 kHz to approximately 100 kHz). The notice trigger pulse indicates that an event marker is about to be transmitted over a second channel (e.g., within a higher frequency range). The event marker can then be transmitted over the second channel.

The event markers may include data indicative of one or more events (e.g., a sensed intrinsic atrial activation for an atrial located LP, a sensed intrinsic ventricular activation for a ventricular located LP). The event markers may include different markers for intrinsic and paced events. The event markers may also indicate start or end times for timers (e.g., an AV interval, a blanking interval, etc.). Optionally, the implant event message may include a message segment that includes additional/secondary information.

Optionally, the LP (or other IMD) that receives any i2i communication signal from another LP (or other IMD) or from an external device may transmit a receive acknowledgement indicating that the receiving LP (or other IMD) received the i2i communication signal. In certain embodiments, where an IMD expects to receive an i2i communication signal within a window, and fails to receive the i2i communication signal within the window, the IMD may transmit a failure-to-receive acknowledgement indicating that the receiving IMD failed to receive the i2i communication signal. Other variations are also possible and within the scope of the embodiments described herein.

The event messages enable the LPs 102a, 102b to deliver synchronized therapy and additional supportive features (e.g., measurements, etc.). To maintain synchronous therapy, each of the LPs 102a and 102b is made aware (through the event messages) when an event occurs in the chamber containing the other LP 102a, 102b. Some embodiments described herein provide efficient and reliable processes to maintain synchronization between LPs 102a and 102b without maintaining continuous communication between LPs 102a and 102b. In accordance with certain embodiments herein, low power event messages/signaling may be maintained between LPs 102a and 102b synchronously or asynchronously.

For synchronous event signaling, LPs 102a and 102b may maintain synchronization and regularly communicate at a specific interval. Synchronous event signaling allows the transmitter and receivers in each LP 102a, 102b to use limited (or minimal) power as each LP 102a, 102b is only powered for a small fraction of the time in connection with transmission and reception. For example, LP 102a, 102b may transmit/receive (Tx/Rx) communication messages in time slots having duration of 10-20 µs, where the Tx/Rx time slots occur periodically (e.g., every 10-20 ms).

LPs 102a and 102b may lose synchronization, even in a synchronous event signaling scheme. As explained herein, features may be included in LPs 102a and 102b to maintain device synchronization, and when synchronization is lost, LPs 102a and 102b undergo operations to recover synchronization. Also, synchronous event messages/signaling may introduce a delay between transmissions which causes a reaction lag at the receiving LP 102a, 102b. Accordingly, features may be implemented to account for the reaction lag.

During asynchronous event signaling, LPs 102a and 102b do not maintain communication synchronization. During asynchronous event signaling, one or more of receivers 120 and 122 of LPs 102a and 102b may be "always on" (always awake) to search for incoming transmissions. However, maintaining LP receivers 120, 122 in an "always on" (always awake) state presents challenges as the received signal level often is low due to high channel attenuation caused by the patient's anatomy. Further, maintaining the receivers awake will deplete the battery 114 more quickly than may be desirable.

The asynchronous event signaling methods avoid risks associated with losing synchronization between devices. However, the asynchronous event signaling methods utilize additional receiver current between transmissions. For purposes of illustration only, a non-limiting example is described hereafter. For example, the channel attenuation may be estimated to have a gain of 1/500 to 1/10000. A gain factor may be 1/1000th. Transmit current is a design factor in addition to receiver current. As an example, the system may allocate one-half of the implant communication current budget to the transmitter (e.g., 0.5 µA for each transmitter). When LP 102a, 102b maintains a transmitter in a continuous on-state and the electrode load is 500 ohms, a transmitted voltage may be 2.5V. When an event signal is transmitted at 2.5V, the event signal is attenuated as it propagates and would appear at LP 102a, 102b receiver as an amplitude of approximately 0.25 mV.

To overcome the foregoing receive power limit, a pulsed transmission scheme may be utilized in which communication transmissions occur correlated with an event. By way of example, the pulsed transmission scheme may be simplified such that each transmission constitutes a single pulse of a select amplitude and width.

In accordance with certain embodiments herein, LPs 102a and 102b may utilize multi-stage receivers that implement a staged receiver wakeup scheme in order to improve reliability yet remain power efficient. Each of LPs 102a and 102b may include first and second receivers 120 and 122 that operate with different first and second activation protocols and different first and second receive channels. For example, first receiver 120 may be assigned a first activation protocol that is "always on" (also referred to as always awake) and that listens over a first receive channel that has a lower fundamental frequency range/pulse duration (e.g., 1 kHz to 100 kHz/10 µs to approximately 1 ms) as compared to the fundamental frequency range (e.g., greater than 100 kHz/ less than 10 µs per pulse) assigned to the second receive channel.

In accordance with certain embodiments, the first receiver 120 may maintain the first channel active (awake) at all times (including when the second channel is inactive (asleep)) in order to listen for messages from a remote LP. The second receiver 122 may be assigned a second activation protocol that is a triggered protocol, in which the second receiver 122 becomes active (awake) in response to detection of trigger events over the first receive channel (e.g., when the incoming signal corresponds to the LP wakeup notice, activating the second channel at the local LP). The terms active, awake and enabled are used interchangeably herein.

Still referring to FIG. 2, each LP 102a, 102b is shown as including a controller 112 and a pulse generator 116. The controller 112 can include, e.g., a microprocessor (or equivalent control circuitry), RAM and/or ROM memory, logic and timing circuitry, state machine circuitry, and I/O circuitry, but is not limited thereto. The controller 112 can further include, e.g., timing control circuitry to control the timing of the stimulation pulses (e.g., pacing rate, atrio-ventricular (AV) delay, atrial interconduction (A-A) delay, or ventricular interconduction (V-V) delay, etc.). Such timing control circuitry may also be used for the timing of refractory periods, blanking intervals, noise detection windows, evoked response windows, alert intervals, marker channel timing, and so on. The controller 112 can further include other dedicated circuitry and/or firmware/software components that assist in monitoring various conditions of the patient's heart and managing pacing therapies. The controller 112 and the pulse generator 116 may be configured to transmit event messages, via the electrodes 108, in a manner that does not inadvertently capture the heart in the chamber where LP 102a, 102b is located, such as when the associated chamber is not in a refractory state. In addition, a LP 102a, 102b that receives an event message may enter an "event refractory" state (or event blanking state) following receipt of the event message. The event refractory/blanking state may be set to extend for a determined period of time after receipt of an event message in order to avoid the receiving LP 102a, 102b from inadvertently sensing another signal as an event message that might otherwise cause retriggering. For example, the receiving LP 102a, 102b may detect a measurement pulse from another LP 102a, 102b or programmer 109.

In accordance with certain embodiments herein, programmer 109 may communicate over a programmer-to-LP channel, with LP 102a, 102b utilizing the same communication scheme. The external programmer may listen to the event message transmitted between LP 102a, 102b and synchronize programmer to implant communication such that programmer 109 does not transmit communication signals 113 until after an implant to implant messaging sequence is completed.

In accordance with certain embodiments, LP 102a, 102b may combine transmit operations with therapy. The transmit event marker may be configured to have similar characteristics in amplitude and pulse-width to a pacing pulse and LP 102a, 102b may use the energy in the event messages to help capture the heart. For example, a pacing pulse may normally be delivered with pacing parameters of 2.5V amplitude, 500 ohm impedance, 60 bpm pacing rate, 0.4 ms pulse-width. The foregoing pacing parameters correspond to a current draw of about 1.9 µA. The same LP 102a, 102b may implement an event message utilizing event signaling parameters for amplitude, pulse-width, pulse rate, etc. that correspond to a current draw of approximately 0.5 µA for transmit.

LP 102a, 102b may combine the event message transmissions with pacing pulses. For example, LP 102a, 102b may use a 50 µs wakeup transmit pulse having an amplitude of 2.5V which would draw 250 nC (nano Coulombs) for an electrode load of 500 ohm. The pulses of the transmit event message may be followed by an event message encoded with a sequence of short duration pulses (for example 16, 2 µs on/off bits) which would draw an additional 80 nC. The event message pulse would then be followed by the remaining pulse-width needed to reach an equivalent charge of a nominal 0.4 ms pace pulse. In this case, the current necessary to transmit the marker is essentially free as it was used to achieve the necessary pace capture anyhow. With this method, the savings in transmit current could be budgeted for the receiver or would allow for additional longevity.

When LP 102a or 102b senses an intrinsic event, it can send a qualitatively similar event pulse sequence (but indicative of a sensed event) without adding the pace pulse remainder. As LP 102a, 102b longevity calculations are designed based on the assumption that LP 102a, 102b will deliver pacing therapy 100% of the time, transmitting an intrinsic event marker to another LP 102a, 102b will not impact the nominal calculated LP longevity.

In some embodiments, LP 102a, 102b may deliver pacing pulses at relatively low amplitude. When low amplitude pacing pulses are used, the power budget for event messages may be modified to be a larger portion of the overall device energy budget. As the pacing pulse amplitude is lowered closer to amplitude of event messages, LP 102a, 102b increases an extent to which LP 102a, 102b uses the event messages as part of the pacing therapy (also referred to as sharing "capture charge" and "transmit charge"). As an example, if the nominal pacing voltage can be lowered to <1.25 V, then a "supply halving" pacing charge circuit could reduce the battery current draw by approximately 50%. A 1.25V pace pulse would save 1.5 µA of pacing current budget. With lower pulse amplitudes, LP 102a, 102b may use larger pulse-widths.

By combining event messages and low power pacing, LP 102a, 102b may realize additional longevity. Today longevity standards provide that the longevity to be specified based on a therapy that utilizes 2.5V amplitude, 0.4 ms pulses at 100% pacing. Optionally, a new standard may be established based on pacing pulses that deliver lower amplitude and/or shorter pacing pulses.

While not shown, a communication capacitor can be provided in LP 102a, 102b. The communication capacitor may be used to transmit event signals having higher voltage for the event message pulses to improve communication, such as when the LPs 102a and 102b experience difficulty sensing event messages. The high voltage event signaling may be used for implants with high signal attenuation or in the case of a retry for an ARQ (automatic repeat request) handshaking scheme.

In some embodiments, the individual LP 102a can comprise a hermetic housing 110 configured for placement on or attachment to the inside or outside of a cardiac chamber and at least two leadless electrodes 108 proximal to the housing 110 and configured for bidirectional communication with at least one other device 106 within or outside the body.

FIG. 2 depicts a single LP 102a (or 102b) and shows the LP's functional elements substantially enclosed in a hermetic housing 110. The LP 102a (or 102b) has at least two electrodes 108 located within, on, or near the housing 110, for delivering pacing pulses to and sensing electrical activity from the muscle of the cardiac chamber, and for bidirectional communication with at least one other device within or outside the body. Hermetic feedthroughs 130, 131 conduct electrode signals through the housing 110. The housing 110 contains a primary battery 114 to supply power for pacing, sensing, and communication. The housing 110 also contains circuits 132 for sensing cardiac activity from the electrodes 108, receivers 120, 122 for receiving information from at least one other device via the electrodes 108, and the pulse generator 116 for generating pacing pulses for delivery via the electrodes 108 and also for transmitting information to at least one other device via the electrodes 108. The housing 110 can further contain circuits for monitoring device health, for example a battery current monitor 136 and a battery voltage monitor 138, and can contain circuits for controlling operations in a predetermined manner.

The electrodes 108 can be configured to communicate bidirectionally among the multiple leadless cardiac pacemakers and/or the implanted ICD 106 to coordinate pacing pulse delivery and optionally other therapeutic or diagnostic features using messages that identify an event at an individual pacemaker originating the message and a pacemaker receiving the message react as directed by the message depending on the origin of the message. An LP 102a, 102b that receives the event message reacts as directed by the event message depending on the message origin or location. In some embodiments or conditions, the two or more leadless electrodes 108 can be configured to communicate bidirectionally among the one or more leadless cardiac pacemakers 102a and/or the ICD 106 and transmit data including designated codes for events detected or created by an individual pacemaker. Individual pacemakers can be configured to issue a unique code corresponding to an event type and a location of the sending pacemaker.

In some embodiments, an individual LP 102a, 102b can be configured to deliver a pacing pulse with an event message encoded therein, with a code assigned according to pacemaker location and configured to transmit a message to one or more other leadless cardiac pacemakers via the event message coded pacing pulse. The pacemaker or pacemakers receiving the message are adapted to respond to the message in a predetermined manner depending on type and location of the event.

Moreover, information communicated on the incoming channel can also include an event message from another leadless cardiac pacemaker signifying that the other leadless cardiac pacemaker has sensed a heartbeat or has delivered a pacing pulse, and identifies the location of the other pacemaker. For example, LP 102b may receive and relay an event message from LP 102a to the programmer. Similarly, information communicated on the outgoing channel can also include a message to another leadless cardiac pacemaker or pacemakers, or to the ICD, that the sending leadless cardiac pacemaker has sensed a heartbeat or has delivered a pacing pulse at the location of the sending pacemaker.

Referring again to FIGS. 1 and 2, the cardiac pacing system 100 may comprise an ICD 106 in addition to one or more LPs 102a, 102b configured for implantation in electrical contact with a cardiac chamber and for performing cardiac rhythm management functions in combination with the implantable ICD 106. The implantable ICD 106 and the one or more LPs 102a, 102b configured for leadless intercommunication by information conduction through body tissue and/or wireless transmission between transmitters and receivers in accordance with the discussed herein.

In a further embodiment, a cardiac pacing system 100 comprises at least one LP 102a, 102b configured for implantation in electrical contact with a cardiac chamber and configured to perform cardiac pacing functions in combination with the co-implanted ICD 106. The leadless cardiac pacemaker or pacemakers 102a comprise at least two leadless electrodes 108 configured for delivering cardiac pacing pulses, sensing evoked and/or natural cardiac electrical signals, and transmitting information to the co-implanted ICD 106.

As shown in the illustrative embodiments, a leadless cardiac pacemaker 102a, 102b can comprise two or more leadless electrodes 108 configured for delivering cardiac pacing pulses, sensing evoked and/or natural cardiac electrical signals, and bidirectionally communicating with the co-implanted ICD 106.

LP 102a, 102b can be configured for operation in a particular location and a particular functionality at manufacture and/or at programming by an external programmer. Bidirectional communication among the multiple leadless cardiac pacemakers can be arranged to communicate notification of a sensed heartbeat or delivered pacing pulse event and encoding type and location of the event to another implanted pacemaker or pacemakers. LP 102a, 102b receiving the communication decode the information and respond depending on location of the receiving pacemaker and predetermined system functionality.

In some embodiments, the LPs 102a and 102b are configured to be implantable in any chamber of the heart, namely either atrium (RA, LA) or either ventricle (RV, LV). Furthermore, for dual-chamber configurations, multiple LPs may be co-implanted (e.g., one in the RA and one in the RV, one in the RV and one in the coronary sinus proximate the LV). Certain pacemaker parameters and functions depend on (or assume) knowledge of the chamber in which the pacemaker is implanted (and thus with which the LP is interacting; e.g., pacing and/or sensing). Some non-limiting examples include sensing sensitivity, an evoked response algorithm, use of AF suppression in a local chamber, blanking & refractory periods, etc. Accordingly, each LP needs to know an identity of the chamber in which the LP is implanted, and processes may be implemented to automatically identify a local chamber associated with each LP.

Processes for chamber identification may also be applied to subcutaneous pacemakers, ICDs, with leads and the like. A device with one or more implanted leads, identification and/or confirmation of the chamber into which the lead was implanted could be useful in several pertinent scenarios. For example, for a DR or CRT device, automatic identification and confirmation could mitigate against the possibility of the clinician inadvertently placing the V lead into the A port of the implantable medical device, and vice-versa. As another example, for an SR device, automatic identification of implanted chamber could enable the device and/or programmer to select and present the proper subset of pacing modes (e.g., AAI or WI), and for the IPG to utilize the proper set of settings and algorithms (e.g., V-AutoCapture vs ACap-Confirm, sensing sensitivities, etc.).

Also shown in FIG. 2, the primary battery 114 has positive terminal 140 and negative terminal 142. Current from the positive terminal 140 of primary battery 114 flows through a shunt 144 to a regulator circuit 146 to create a positive voltage supply 148 suitable for powering the remaining circuitry of the pacemaker 102. The shunt 144 enables the battery current monitor 136 to provide the processor 112 with an indication of battery current drain and indirectly of device health. The illustrative power supply can be a primary battery 114.

Referring to FIG. 2, the LP is shown as including a temperature sensor 152. The temperature sensor can be any one of various different types of well-known temperature sensors, or can be a future developed temperature sensor. For one example, the temperature sensor 152 can be a thermistor, a thermocouple, a resistance thermometer, or a silicon bandgap temperature sensor, but is not limited thereto. Regardless of how the temperature sensor 152 is implemented, it is preferably that the temperature sensed by the sensor is provided to the controller 112 as a digital signal indicative of the blood temperature of the patient within which the LP is implanted. The temperature sensor 152 can be hermetically sealed within the housing 110, but that need not be the case. The temperature sensor 152 can be used in various manners. For example, the temperature sensor 152 can be used to detect an activity level of the patient to adjust a pacing rate, i.e., for use in rate responsive pacing. When a person starts to exercise their core body temperature initially dips, and then after exercising for a prolonged period of time the person's core body temperature will eventually rise. Thereafter, when the person stops exercising their core body temperature will return to its baseline. Accordingly, the controller 112 can be configured to detect an activity level of a patient based on core blood temperature measurements obtained using the temperature sensor 152.

Referring to FIG. 2, the LP is also shown as including an accelerometer 154 which can be hermetically contained within the housing 110. The accelerometer 154 can be any one of various different types of well-known accelerometers, or can be a future developed accelerometer. For one example, the accelerometer 154 can be or include, e.g., a MEMS (micro-electromechanical system) multi-axis accelerometer of the type exploiting capacitive or optical cantilever beam techniques, or a piezoelectric accelerometer that employs the piezoelectric effect of certain materials to measure dynamic changes in mechanical variables. For example, the accelerometer 154 can be used to detect an activity level of the patient to adjust a pacing rate, i.e., for use in rate responsive pacing. It would also be possible to use outputs of both the accelerometer 154 and the temperature sensor 152 to monitor the activity level of a patient. Alternatively, or additionally, a patient's activity level can be monitored based on their heart rate, as detected from an IEGM sensed using the electrodes 108, and/or sensed using a plethysmography signal obtained using a plethysmography sensor (not shown) or a heart sound sensor (not shown), but not limited thereto. One or more signals produced and output by the accelerometer 154 may be analyzed with respect to frequency content, energy, duration, amplitude and/or other characteristics. Such signals may or may not be amplified and/or filtered prior to being analyzed. For example, filtering may be performed using lowpass, highpass and/or bandpass filters. The signals output by the accelerometer 154 can be analog signals, which can be analyzed in the analog domain, or can be converted to digital signals (by an analog-to-digital converter) and analyzed in the digital domain. Alternatively, the signals output by the accelerometer 154 can already be in the digital domain. The one or more signals output by the accelerometer 154 can be analyzed by the controller 112 and/or other circuitry. In certain embodiments, the accelerometer 154 is packaged along with an integrated circuit (IC) that is designed to analyze the signal(s) it generates. In such embodiments, one or more outputs of the packaged sensor/IC can be an indication of acceleration along one or more axes. In other embodiments, the accelerometer 154 can be packaged along with an IC that performs signal conditioning (e.g., amplification and/or filtering), performs analog-to-digital conversions, and stores digital data (indicative of the sensor output) in memory (e.g., RAM, which may or may not be within the same package). In such embodiments, the controller 112 or other circuitry can read the digital data from the memory and analyze the digital data. Other variations are also possible, and within the scope of embodiments of the present technology. In accordance with certain embodiments of the present technology, described in additional detail below, a sensor signal produced by the accelerometer 154 of an LP implanted in or on a cardiac chamber can be used to detect mechanical cardiac activity associated with another cardiac chamber.

In various embodiments, LP 102a, 102b can manage power consumption to draw limited power from the battery, thereby reducing device volume. Each circuit in the system can be designed to avoid large peak currents. For example, cardiac pacing can be achieved by discharging a tank capacitor (not shown) across the pacing electrodes. Recharging of the tank capacitor is typically controlled by a charge pump circuit. In a particular embodiment, the charge pump circuit is throttled to recharge the tank capacitor at constant power from the battery.

In some embodiments, the controller 112 in one leadless cardiac pacemaker 102a can access signals on the electrodes 108 and can examine output pulse duration from another pacemaker for usage as a signature for determining triggering information validity and, for a signature arriving within predetermined limits, activating delivery of a pacing pulse following a predetermined delay of zero or more milliseconds. The predetermined delay can be preset at manufacture, programmed via an external programmer, or determined by adaptive monitoring to facilitate recognition of the triggering signal and discriminating the triggering signal from noise. In some embodiments or in some conditions, the controller 112 can examine output pulse waveform from another leadless cardiac pacemaker for usage as a signature for determining triggering information validity and, for a signature arriving within predetermined limits, activating delivery of a pacing pulse following a predetermined delay of zero or more milliseconds.

FIG. 2 shows an LP 102a, 102b. The LP can include a hermetic housing 202 with electrodes 108a and 108b disposed thereon. As shown, electrode 108a can be separated from but surrounded partially by a fixation mechanism 205, and the electrode 108b can be disposed on the housing 202. The fixation mechanism 205 can be a fixation helix, a plurality of hooks, barbs, or other attaching features configured to attach the pacemaker to tissue, such as heart tissue. The electrodes 108a and 108b are examples of the electrodes 108 shown in and discussed above with reference to FIG. 2.

The housing can also include an electronics compartment 210 within the housing that contains the electronic components necessary for operation of the pacemaker, including, e.g., a pulse generator, receiver, a battery, and a processor for operation. The hermetic housing 202 can be adapted to be implanted on or in a human heart, and can be cylindrically shaped, rectangular, spherical, or any other appropriate shapes, for example.

The housing can comprise a conductive, biocompatible, inert, and anodically safe material such as titanium, 316L stainless steel, or other similar materials. The housing can further comprise an insulator disposed on the conductive material to separate electrodes 108a and 108b. The insulator can be an insulative coating on a portion of the housing between the electrodes, and can comprise materials such as silicone, polyurethane, parylene, or another biocompatible electrical insulator commonly used for implantable medical devices. In the embodiment of FIG. 2, a single insulator 208 is disposed along the portion of the housing between electrodes 108a and 108b. In some embodiments, the housing itself can comprise an insulator instead of a conductor, such as an alumina ceramic or other similar materials, and the electrodes can be disposed upon the housing.

As shown in FIG. 2, the pacemaker can further include a header assembly 212 to isolate 108a and 108b. The header assembly 212 can be made from PEEK, tecothane or another biocompatible plastic, and can contain a ceramic to metal feedthrough, a glass to metal feedthrough, or other appropriate feedthrough insulator as known in the art.

The electrodes 108a and 108b can comprise pace/sense electrodes, or return electrodes. A low-polarization coating can be applied to the electrodes, such as sintered platinum, platinum-iridium, iridium, iridium-oxide, titanium-nitride, carbon, or other materials commonly used to reduce polarization effects, for example. In FIG. 2, electrode 108a can be a pace/sense electrode and electrode 108b can be a return electrode. The electrode 108b can be a portion of the conductive housing 202 that does not include an insulator 208.

Several techniques and structures can be used for attaching the housing 202 to the interior or exterior wall of the heart. A helical fixation mechanism 205, can enable insertion of the device endocardially or epicardially through a guiding catheter. A torqueable catheter can be used to rotate the housing and force the fixation device into heart tissue, thus affixing the fixation device (and also the electrode 108a in FIG. 2) into contact with stimulable tissue. Electrode 108b can serve as an indifferent electrode for sensing and pacing. The fixation mechanism may be coated partially or in full for electrical insulation, and a steroid-eluting matrix may be included on or near the device to minimize fibrotic reaction, as is known in conventional pacing electrode-leads.

Implant-to-Implant Event Messaging

LPs 102a and 102b can utilize implant-to-implant (i2i) communication through event messages to coordinate operation with one another in various manners. The terms i2i communication, i2i event messages, and i2i event markers are used interchangeably herein to refer to event related messages and IMD/IMD operation related messages transmitted from an implanted device and directed to another implanted device (although external devices, e.g., a programmer, may also receive i2i event messages). In certain embodiments, LP 102a and LP 102b operate as two independent leadless pacers maintaining beat-to-beat dual-chamber functionality via a "Master/Slave" operational configuration. For descriptive purposes, the ventricular LP 102b shall be referred to as "vLP" and the atrial LP 102a shall be referred to as "aLP". The LP 102 that is designated as the master device (e.g. vLP) may implement all or most dual-chamber diagnostic and therapy determination algorithms. For purposes of the following illustration, it is assumed that the vLP is a "master" device, while the aLP is a "slave" device. Alternatively, the aLP may be designated as the master device, while the vLP may be designated as the slave device. The master device orchestrates most or all decision-making and timing determinations (including, for example, rate-response changes).

In accordance with certain embodiments, methods are provided for coordinating operation between first and second leadless pacemakers (LPs) configured to be implanted entirely within first and second chambers of the heart. A method transmits an event marker through conductive communication through electrodes located along a housing of the first LP, the event marker indicative of one of a local paced or sensed event. The method detects, over a sensing channel, the event marker at the second LP. The method identifies the event marker at the second LP based on a predetermined pattern configured to indicate that an event of interest has occurred in a remote chamber. In response to the identifying operation, the method initiates a related action in the second LP.

Figure 4:
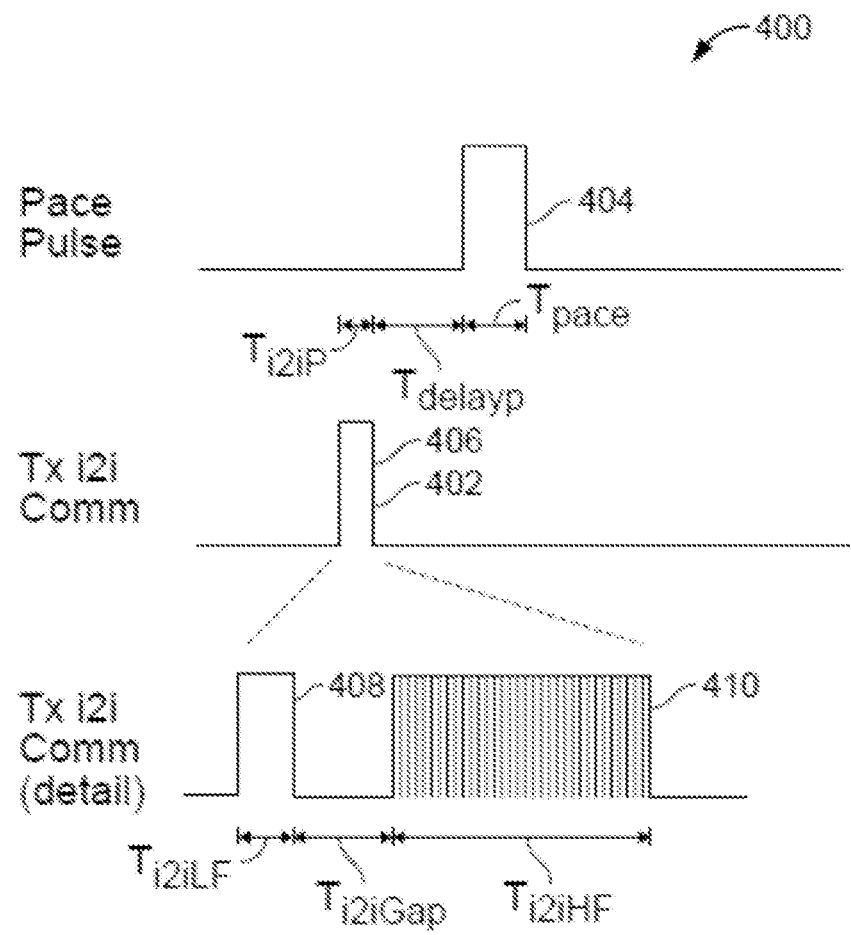
FIG. 4 is a timing diagram demonstrating one embodiment of implant to implant (i2i) communication for a paced event.

FIG. 4 is a timing diagram 400 demonstrating one example of an i2i communication for a paced event. The i2i communication may be transmitted, for example, from LP 102a to LP 102b. As shown in FIG. 4, in this embodiment, an i2i transmission 402 is sent prior to delivery of a pace pulse 404 by the transmitting LP (e.g., LP 102). This enables the receiving LP (e.g., LP 102b) to prepare for the remote delivery of the pace pulse. The i2i transmission 402 includes an envelope 406 that may include one or more individual pulses. For example, in this embodiment, envelope 406 includes a low frequency pulse 408 followed by a high frequency pulse train 410. Low frequency pulse 408 lasts for a period $T_{i2iLF}$, and high frequency pulse train 410 lasts for a period $T_{i2iHF}$. The end of low frequency pulse 408 and the beginning of high frequency pulse train 410 are separated by a gap period, $T_{i2iGap}$.

As shown in FIG. 4, the i2i transmission 402 lasts for a period Ti2iP, and pace pulse 404 lasts for a period Tpace. The end of i2i transmission 402 and the beginning of pace pulse 404 are separated by a delay period, TdelayP. The delay period may be, for example, between approximately 0.0 and 10.0 milliseconds (ms), particularly between approximately 0.1 ms and 2.0 ms, and more particularly approximately 1.0 ms. The term approximately, as used herein, means+/−10% of a specified value.

Figure 5:
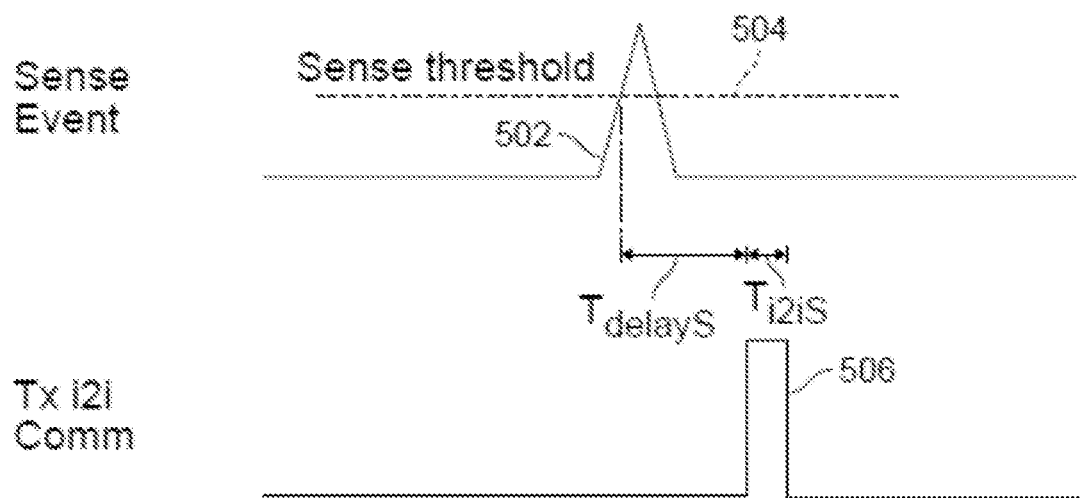
FIG. 5 is a timing diagram demonstrating one embodiment of i2i communication for a sensed event.

FIG. 5 is a timing diagram 500 demonstrating one example of an i2i communication for a sensed event. The i2i communication may be transmitted, for example, from LP 102a to LP 102b. As shown in FIG. 5, in this embodiment, the transmitting LP (e.g., LP 102a) detects the sensed event when a sensed intrinsic activation 502 crosses a sense threshold 504. A predetermined delay period, $T_{delayS}$, after the detection, the transmitting LP transmits an i2i transmission 506 that lasts a predetermined period $T_{i2iS}$. The delay period may be, for example, between approximately 0.0 and 10.0 milliseconds (ms), particularly between approximately 0.1 ms and 2.0 ms, and more particularly approximately 1.0 ms.

As with i2i transmission 402, i2i transmission 506 may include an envelope that may include one or more individual pulses. For example, similar to envelope 406, the envelope of i2i transmission 506 may include a low frequency pulse followed by a high frequency pulse train.

Optionally, wherein the first LP is located in an atrium and the second LP is located in a ventricle, the first LP produces an AS/AP event marker to indicate that an atrial sensed (AS) event or atrial paced (AP) event has occurred or will occur in the immediate future. For example, the AS and AP event markers may be transmitted following the corresponding AS or AP event. Alternatively, the first LP may transmit the AP event marker slightly prior to delivering an atrial pacing pulse. Alternatively, wherein the first LP is located in an atrium and the second LP is located in a ventricle, the second LP initiates an atrioventricular (AV) interval after receiving an AS or AP event marker from the first LP; and initiates a post atrial ventricular blanking (PAVB) interval after receiving an AP event marker from the first LP.

Optionally, the first and second LPs may operate in a "pure" master/slave relation, where the master LP delivers "command" markers in addition to or in place of "event" markers. A command marker directs the slave LP to perform an action such as to deliver a pacing pulse and the like. For example, when a slave LP is located in an atrium and a master LP is located in a ventricle, in a pure master/slave relation, the slave LP delivers an immediate pacing pulse to the atrium when receiving an AP command marker from the master LP.

In accordance with some embodiments, communication and synchronization between the aLP and vLP is implemented via conducted communication of markers/commands in the event messages (per i2i communication protocol). As explained above, conducted communication represents event messages transmitted from the sensing/pacing electrodes at frequencies outside the RF or Wi-Fi frequency range. Alternatively, the event messages may be conveyed over communication channels operating in the RF or Wi-Fi frequency range. The figures and corresponding description below illustrate non-limiting examples of markers that may be transmitted in event messages. The figures and corresponding description below also include the description of the markers and examples of results that occur in the LP that receives the event message. Table 1 represents exemplary event markers sent from the aLP to the vLP, while Table 2 represents exemplary event markers sent from the vLP to the aLP. In the master/slave configuration, AS event markers are sent from the aLP each time that an atrial event is sensed outside of the post ventricular atrial blanking (PVAB) interval or some other alternatively-defined atrial blanking period. The AP event markers are sent from the aLP each time that the aLP delivers a pacing pulse in the atrium. The aLP may restrict transmission of AS markers, whereby the aLP transmits AS event markers when atrial events are sensed both outside of the PVAB interval and outside the post ventricular atrial refractory period (PVARP) or some other alternatively-defined atrial refractory period. Alternatively, the aLP may not restrict transmission of AS event markers based on the PVARP, but instead transmit the AS event marker every time an atrial event is sensed.

TABLE 1

"A2V" Markers/Commands (i.e., from aLP to vLP)

| Marker | Description | Result in vLP |
|---|---|---|
| AS | Notification of a sensed event in atrium (if not in PVAB or PVARP) | Initiate AV interval (if not in PVAB or PVARP) |
| AP | Notification of a paced event in atrium | Initiate PAVB Initiate AV interval (if not in PVARP) |

As shown in Table 1, when an aLP transmits an event message that includes an AS event marker (indicating that the aLP sensed an intrinsic atrial event), the vLP initiates an AV interval timer. If the aLP transmits an AS event marker for all sensed events, then the vLP would preferably first determine that a PVAB or PVARP interval is not active before initiating an AV interval timer. If however the aLP transmits an AS event marker only when an intrinsic signal is sensed outside of a PVAB or PVARP interval, then the vLP could initiate the AV interval timer upon receiving an AS event marker without first checking the PVAB or PVARP status. When the aLP transmits an AP event marker (indicating that the aLP delivered or is about to deliver a pace pulse to the atrium), the vLP initiates a PVAB timer and an AV interval time, provided that a PVARP interval is not active. The vLP may also blank its sense amplifiers to prevent possible crosstalk sensing of the remote pace pulse delivered by the aLP.

TABLE 2

"V2A" Markers/Commands (i.e., from vLP to aLP)

| Marker | Description | Result in aLP |
|---|---|---|
| VS | Notification of a sensed event in ventricle | Initiate PVARP |
| VP | Notification of a paced event in ventricle | Initiate PVAB Initiate PVARP |
| AP | Command to deliver immediate pace pulse in atrium | Deliver immediate pace pulse to atrium |

As shown in Table 2, when the vLP senses a ventricular event, the vLP transmits an event message including a VS event marker, in response to which the aLP may initiate a PVARP interval timer. When the vLP delivers or is about to deliver a pace pulse in the ventricle, the vLP transmits VP event marker. When the aLP receives the VP event marker, the aLP initiates the PVAB interval timer and also the PVARP interval timer. The aLP may also blank its sense amplifiers to prevent possible crosstalk sensing of the remote pace pulse delivered by the vLP. The vLP may also transmit an event message containing an AP command marker to command the aLP to deliver an immediate pacing pulse in the atrium upon receipt of the command without delay.

The foregoing event markers are examples of a subset of markers that may be used to enable the aLP and vLP to maintain full dual chamber functionality. In one embodiment, the vLP may perform all dual-chamber algorithms, while the aLP may perform atrial-based hardware-related functions, such as PVAB, implemented locally within the aLP. In this embodiment, the aLP is effectively treated as a remote 'wireless' atrial pace/sense electrode. In another embodiment, the vLP may perform most but not all dual-chamber algorithms, while the aLP may perform a subset of diagnostic and therapeutic algorithms. In an alternative embodiment, vLP and aLP may equally perform diagnostic and therapeutic algorithms. In certain embodiments, decision responsibilities may be partitioned separately to one of the aLP or vLP. In other embodiments, decision responsibilities may involve joint inputs and responsibilities.

In an embodiment, ventricular-based pace and sense functionalities are not dependent on any i2i communication, in order to provide safer therapy. For example, in the event that LP to LP (i2i) communication is lost (prolonged or transient), the system 100 may automatically revert to safe ventricular-based pace/sense functionalities as the vLP device is running all of the necessary algorithms to independently achieve these functionalities. For example, the vLP may revert to a WI mode as the vLP does not depend on i2i communication to perform ventricular pace/sense activities. Once i2i communication is restored, the system 100 can automatically resume dual-chamber functionalities.

Messages that are transmitted between LPs (e.g., the aLP and the vLP) can be referred to herein generally as i2i messages, since they are implant-to-implant messages. As noted above, such messages can include event markers that enable one LP to inform the other LP of a paced event or a sensed event. For example, in certain embodiments, whenever the aLP senses an atrial event or paces the right atrium, the aLP will transmit an i2i message to the vLP to inform the vLP of the sensed or paced event in the atrium. In response to receiving such an i2i message, the vLP may start one or more timers that enable the vLP to sense or pace in the right ventricle. Similarly, the vLP may transmit an i2i message to the aLP whenever the vLP senses a ventricular event or paces the right ventricle.

The i2i messages that are sent between LPs may be relatively short messages that simply allow a first LP to inform a second LP of an event that was sensed by the first LP or caused (paced) by the first LP, and vice versa. Such i2i messages can be referred to herein as event marker i2i messages, or more succinctly as event i2i messages. The i2i messages that are sent between LPs, in certain instances, can be extended i2i messages that include (in addition to an event marker) an extension. In certain embodiments, an extended i2i message includes an event marker (e.g., 9 bits), followed by an extension indicator (e.g., 2 bits), followed by an extended message payload portion (e.g., 17 bits), followed by a cyclic redundancy check (CRC) code (e.g., 6 bits) or some other type of error detection and correction code.

In certain embodiments, whenever an i2i message is sent by an LP (or other type of IMD, such as a S-ICD), the i2i message will include an extension indicator so that the receiving LP knows whether or not the i2i message it receives includes an extension portion. In such embodiments, even a relatively short event i2i message will include an extension indicator. The extension indicator (e.g., 2 bits) is used by the LP (or other IMD) sending the i2i message to indicate, to the LP receiving the i2i message, whether or not the i2i message is an extended i2i message. In certain embodiments, if the LP receiving an i2i message determines based on the extension indicator bits that the received i2i message is not an extended i2i message, then the LP receiving the i2i message can ignore any bits that follow the extension bits. In such a case, the LP receiving the i2i message only decodes the event marker. On the other hand, if the LP receiving an i2i message determines based on the extension indicator bits that the received i2i message is an extended i2i message, then the LP receiving the i2i message will also decode the bits that follow the extension bits, and determine based on a CRC code (or other type of error detection and correction code), whether the i2i message is a valid message. If the extended i2i message is a valid i2i message, then the LP receiving the extended i2i message will as appropriate modify its operation, update parameters, and/or the like, based on information included in the extended i2i message. In certain embodiments, event i2i messages that are not extended i2i messages do not include any error detection and correction code.

In an extended i2i message, the event marker bits and the extension indicator bits are located, respectively, in an event marker field and an extension indicator field of an i2i message packet. In certain embodiments, the extended portion (that follows the event marker bits and the extension indicator bits) includes message bits (in a message field) and rate indicator bits (in a rate indicator field), which are parts of the payload. The payload can alternatively, or additionally, include other types of fields, such as an acknowledgement field that is used in certain situations for one LP to acknowledge reception of an i2i message from another LP of certain (e.g., critical) types of message.

More generally, various different types of information may be included within the payload of an extended i2i message. For one example, the payload can include a pacing rate indicator that enables one LP to inform another LP of a pacing rate. For example, assume that an LP system provides rate responsive pacing, wherein a pacing rate is adjusted in dependence on a patient's physical activity as detected, e.g., using an accelerometer, temperature sensor, and/or other type of sensor of an LP. In such an LP system, the vLP may inform the aLP of the rate at which the patient's heart should be paced so that the aLP and vLP can perform synchronized pacing. To achieve this, the vLP can send a pacing rate indicator to the aLP in the payload of an extended i2i message. The pacing rate indicator can, e.g., be a value indicating a pacing rate value (e.g., 80 bpm), a code that the aLP that can look up (e.g., in a stored look up table) and corresponds to a pacing rate value, or a value that the aLP feeds into an equation to determine the pacing rate, but is not limited thereto. Alternatively, the pacing rate indicator can be beat-to-beat interval value (e.g., 0.75 seconds), a code that the aLP can look up and corresponds to a beat-to-beat interval value, or a value that the aLP feeds into an equation to determine the beat-to-beat interval, but is not limited thereto. Other variations are also possible and within the scope of the embodiments described herein.

False Messages

As noted above, implantable medical devices and systems often rely on proper communication to operate correctly. For example, in a dual leadless cardiac pacemaker system, such as the one described above with reference to FIGS. 1-5, i2i communication is critical for proper synchronization of the system. However, noise may cause one or more devices of such a system to falsely detect an i2i message and inappropriately respond thereto. For example, an atrial LP may falsely detect a message from a ventricular LP, wherein the false message includes a portion which the atrial LP mistakenly decodes as a pacing rate indicator that causes the atrial LP to pace the right atrium at an inappropriate high-rate. As also noted above, to reduce the chances of false message, such messages can include redundant data for error detection and correction. However, due to the desire to keep the power consumption low, the messaging and/or error correction and detection scheme may be simple and false messages may still get through.

Certain embodiments of the present technology described herein can be used to reduce how often an IMD, such as a vLP (e.g., 102*b*) or an aLP (e.g., 102*a*), accept false messages. Additionally, or alternatively, certain embodiments of the present technology can be used to mitigate the adverse effects of an IMD accepting one or more false messages.

When a message is accepted by an IMD, the IMD may trigger a timer, trigger an event and/or otherwise be responsive to the message to control or provide an instruction to the IMD that received the message. By contrast, when a message is rejected, this means that the message is prevented (e.g., blocked) from being used to trigger a timer, trigger an event and/or otherwise being used to control or provide an instruction to the IMD that received the message.

The term "message", as used herein, can refer to an actual sent message that is received and is capable of being decoded by an IMD, an actual sent message that is received but is too noisy to be decoded by the IMD, an actual sent message that is received but due to noise it is decoded mistakenly for a different message, noise that is received and is initially mistaken for being an actual message but cannot be decoded by the IMD because it is sufficiently different than an actual message, as well as noise that is received and is mistaken for being an actual message and is decoded by the IMD because it is sufficiently similar than an actual message. The term "false message", as used herein, refers to noise that is received and decoded by the IMD and is mistaken for being an actual message because it is sufficiently similar to an actual message. The term "false message", as used herein, can also refer to an actual sent message that is received but due to noise it is decoded mistakenly for a different message. The term "true message", as used herein, refers to an actual sent message that is received by an IMD and is correctly decoded by the IMD. An actual sent message may have been sent by another IMD, or alternatively, by a non-implanted device, such as a programmer (e.g., 109). Where an actual sent message includes multiple parts, it is possible that a first part of a received message is correctly decoded and a second part of the received message is incorrectly decoded, in which case it can be said that first part of the received message is a "true sub-message" and the second part of the received message is a "false sub-message."

In a system that includes an aLP (e.g., 102*a*) and a vLP (e.g., 102*b*), which are intended to provide for coordinated (aka synchronized) pacing of atrial and ventricular cardiac chambers, false messages could potentially cause the aLP and the vLP to become unsynchronized to the point that it takes a significant amount of time for the aLP and vLP to become resynchronized, or to the point that they could not become resynchronized. For example, if the aLP receives a false message that instructs the aLP to pace at a high rate (e.g., 110 bpm), when the vLP is actually pacing at a low rate (e.g., 60 bpm), the aLP will pace the right atrium at a much higher rate than the vLP is pacing the right ventricle. When pacing at the high rate, the aLP will search for messages from the vLP at a high rate, but the vLP will still send messages at the low rate. If the rate difference is sufficiently large, there may never be an opportunity for the aLP and the vLP to sync back up, and the aLP and the vLP being out of sync with one another can continue indefinitely. In this situation, the vLP device can no longer correct the incorrect high rate being used by the aLP. In certain implementations, during this time the system will go into "safe mode", and the aLP will stop pacing indefinitely. The problem of the aLP and the vLP not being able to sync back up with one another can be referred to herein as the "lock-up" problem.

The above described "lock-up" problem may occur, e.g., where the aLP receives a false i2i message that instructs the aLP to pace at a much higher rate than the vLP is pacing, or where the vLP receives a false i2i message that instructs the vLP to pace at a much higher rate than the aLP is pacing. The so called "lock-up" problem may also occur for various other reasons, discussed below, some of which relate to an LP receiving a false message, and others of which relate to an LP failing to receive a sent message. For example, if the vLP sends an i2i message to the aLP that informs the aLP that it should pace at a much higher rate than it had been (and assuming the vLP itself increases its rate to that much higher rate), if the aLP fails to receive that i2i message and thus does not increase its pacing rate, then the aLP may pace at a rate much lower than the vLP, potentially preventing the aLP and the vLP from being able to sync back up with one another again.

Examples of other types of i2i message that if missed could potentially cause the above described "lock-out" problem are i2i messages that include, for example, a recommended replacement time (RRT) indicator, or an automatic mode switch (AMS) entry indicator, an AMS exit indicator, a magnet entry indicator, or a magnet exit indicator. Each of these indicators are discussed below, along with an explanation of how failing to receive an i2i message including such an indicator could potentially cause the above described "lock-out" problem.

In accordance with certain embodiments, when the aLP detects atrial flutter (AFl) or atrial fibrillation (AF), the aLP will trigger an automatic mode switching (AMS). Auto Mode Switching (AMS) is a standard dual-chamber pacemaker feature that, upon detection of a high atrial rate (e.g., during atrial fibrillation or flutter), provides automatic transition from an AV synchronous pacing mode to one without atrial tracking so as to avoid non-physiologically high ventricular rates that might otherwise result in adverse/symptomatic hemodynamic cardiac performance. Conversely, when the high atrial rate reverts to a more physiologic rate, AMS functionality will terminate and the pacemaker system will again transition back to an AV synchronous pacing mode. Furthermore, pacemaker systems may utilize these AMS entry and exit events as triggers to initiate additional actions, such as collecting diagnostic data, storing intracardiac electrograms, etc.

With the use of two independent LPs (e.g., a vLP and an aLP) operating in a dual-chamber mode, it may be desirable that the LPs respond to AMS entry and exit events in a consistent and synchronized manner (assuming that AMS functionality is available and selected). One means to accomplish this response synchronization is to send a special message from a first LP (e.g., the aLP) to a second LP (e.g., the vLP) that indicates that the threshold for AMS entry or exit has been met. Since AMS entry/exit thresholds relate to atrial rates, a preferred implementation would be to have the aLP be directly responsible for determining AMS transitions, with the aLP then communicating that transition event to the vLP via a special message. Alternatively, the vLP could be responsible for determining AMS transitions via monitoring of the rate at which it receives atrial sense (AS) atrial-to-ventricular (A2V) i2i markers.

Since the underlying high atrial rate could persist for a relatively long and undetermined duration, an exemplary embodiment includes sending AMS special messages (e.g., an "AMS Entry" special message) from the first LP to the second LP upon reaching the AMS entry trigger, and then sending a separate CAMS Exit' special message upon reaching the AMS exit trigger. In other words, an aLP can send an i2i message that includes an AMS entry indicator to the vLP whenever the aLP enters an AMS mode, and the aLP can send an i2i message to the vLP whenever the aLP exits the AMS mode. If the vLP receives a false i2i message that includes what the vLP decodes as an AMS entry indicator, the vLP and the aLP may become out of sync with one another, potentially resulting in the above described lock-up problem where the aLP and the vLP are unable to sync back up with one another.

It is likely that the separate and independent LPs will reach their individual recommended replacement times (RRT) at different points in their lifetimes (e.g., due to different initial battery capacities, different pacing output levels or burdens, etc.). However, it may be desirable or important for the dual-chamber system to react synchronously to the realization of RRT by either LP. For example, it may be desirable to turn off rate-responsiveness upon reaching RRT. As another example, it may be desirable to reduce the base rate upon reaching RRT. Modification of other features might also be considered. One means to accomplish this RRT response synchronization is to send a special message from a first LP to a second LP that indicates that the RRT threshold has been reached in the first LP. In other words, a first LP may send an i2i message including an RRT reached indicator to a second LP when the first LP reaches its RRT. The second LP, in response to receiving the RRT reached indicator from the first LP, may turn off certain types of circuitry and/or functionality. If a first LP receives a false i2i message that includes what the first LP decodes as an RRT reached indicator that it believes was sent by a second LP, then this may cause the first and second LPs (e.g., the vLP and the aLP) to become out of sync with one another, potentially resulting in the above described lock-out problem.

A magnet externally-applied to a patient that has been implanted with an IMD (e.g., pacemaker, ICD, etc.) is a standard means to (a) immediately initiate non-inhibited fixed-rate pacing (e.g., DOO, VOO, or AOO mode, as appropriate), and/or (b) provide a quick means to assess the IMD's battery status (via a standardized pattern of induced pacing rates). With the use of two independent LPs operating in a dual-chamber mode, it is desirable that these LPs respond to an applied magnet in a consistent and synchronized manner (assuming that Magnet Mode functionality is available and selected). One means to accomplish this response synchronization is to send a special message from a first LP to a second LP indicating that a magnet has been (or is being) actively detected by the first LP. In other words, a first LP that detects a magnet can send an i2i message including a magnet detection indicator to a second LP to indicate initial detection of the magnet by the first LP, and then a separate i2i message could be sent to indicate loss of detection of that magnet by the first LP. Upon detection of the applied magnet by the first LP and receipt of the i2i message including the magnet detection indicator by the second LP, the LPs could immediately and synchronously initiate the appropriate pre-defined or programmed Magnet Mode protocol. For example, the LPs could immediately transition from their programmed dual-chamber functional mode (e.g., DDDR) to the defined non-inhibited fixed-rate magnet mode (e.g., DOO or VOO). Furthermore, the pattern and/or rate of pacing output could conform to the defined magnet mode protocol (e.g., per AAMI PC88). The magnet mode settings could be maintained by both LPs until the magnet is no longer detected, at which point the LPs would synchronously revert to their normal mode and functionality. If a first LP receives a false i2i message that includes what the first LP decodes as a magnet detection indicator that it believes was sent by a second LP, then this may cause the first and second LPs (e.g., the vLP and the aLP) to become out of sync with one another, potentially resulting in the above described lock-out problem.

Various embodiments of the present technology, described herein, can be used to prevent or reduce the probability of the above described "lock-up" problem occurring. Additionally, or alternatively, various embodiments of the present technology described herein can be used to mitigate the adverse effects of false messages, should they occur. These various embodiments, described herein, can be used alone or in combination with one another. For example, one, two, or more of the below described embodiments can be implemented.

Slew Rate Protection

In accordance with certain embodiments of the present technology, which are for use with a system including two or more LPs, whenever a first LP receives an i2i message from a second LP, which message instructs the second LP to increases its pacing rate beyond a threshold amount, the second LP limits its increase to the threshold amount which is set at some level that prevents the LPs from getting too far out of synchronization with one another. With such embodiments, if there is indeed a need for a pacing rate increase to occur beyond the threshold amount, the increase would need to occur gradually, rather than all at once, so as to avoid the above described "lock-up" problem. Such embodiments can be referred to as the slew rate protection embodiments since they limit the rate at which one LP may increase its pacing rate in response to a message, which may (or may not) be a false message. Such embodiments can also be used where one or more LPs are configured to adjust their pacing rate in response to i2i messages including pacing rate indicators transmitted by another type of IMD, such as an S-ICD, but not limited thereto. More generally, such embodiments, which are described in additional detail below with reference to the high level flow diagram of FIG. 6A, are for use by a leadless pacemaker (LP) implanted in or on a first cardiac chamber of a patient that also has an implantable medical device (IMD) remotely located relative to the LP, wherein the LP is configured to pace the first cardiac chamber (e.g., the right atrial chamber, or the right ventricular chamber) and adjust a pacing rate at which the first cardiac chamber is paced based on a pacing rate indicator included in an i2i message received from the IMD (e.g., another LP, or an S-ICD).

Figure 6A:
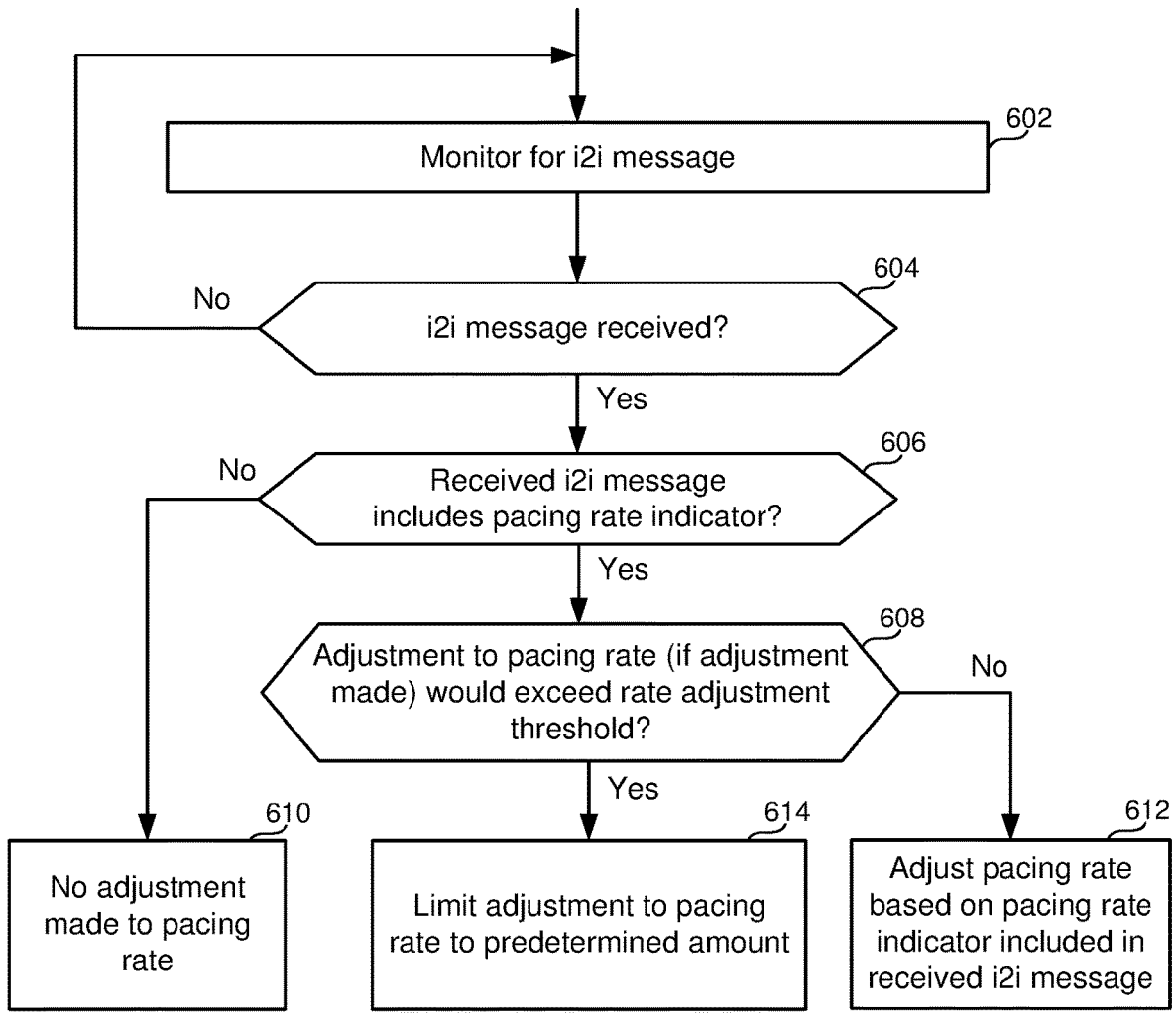
FIG. 6A is a high level flow diagram that is used to summarize methods for providing slew rate protection, according to certain embodiments of the present technology.

Referring to FIG. 6A, step 602 involves the LP monitoring for i2i messages. The LP that performs step 602 can be, e.g., the aLP 102a implanted in (or on) the right atrial chamber, but is not limited thereto. The i2i messages being monitored for at step 602 can be i2i messages that are transmitted by another LP (e.g., the vLP 102b implanted in or on the right ventricular chamber) or by an S-ICD (e.g., 106), but is not limited thereto. Such i2i messages that are monitored for can include extended i2i messages that include a pacing rate indicator within their payload. One or more receivers (e.g., 120 and/or 122) of an LP can be used to perform step 602. Such receiver(s) can be connected to electrodes (e.g., 108) where the i2i messages are conductive communication type messages, or can be connected to an antenna (e.g., 128) where the i2i messages are RF communication type messages.

Still referring to FIG. 6A, at step 604 there is a determination of whether an i2i message is received. If an i2i message is determined to have not been received, then flow returns to step 602 and the LP continues to monitor for an i2i message. If an i2i message is determined to have been received, then flow goes to step 606. The message that is determined to have been received at step 604 may not actually be a true message, but rather, may be a false message.

The types of messages that may be received include relatively simple event marker i2i messages that do not include a pacing rate indicator, or extended i2i messages that may include a pacing rate indicator. As noted above, such extended i2i messages may include error detection and correction codes, such as CRC codes. Accordingly, step 602 and/or 604 can involve performing error detection and correction.

At step 606 there is a determination of whether the received i2i message includes a pacing rate indicator. As noted above, a pacing rate indicator can, e.g., be a value indicating a pacing rate value (e.g., 80 bpm), a code that an LP can look up (e.g., in a stored look up table) and corresponds to a pacing rate value, or a value that an LP feeds into an equation to determine the pacing rate, but is not limited thereto. Alternatively, the pacing rate indicator can be beat-to-beat interval value (e.g., 0.75 seconds), a code that the LP can look up and corresponds to a beat-to-beat interval value, or a value that the LP feeds into an equation to determine the beat-to-beat interval, but is not limited thereto. Other variations are also possible and within the scope of the embodiments described herein. For another example, the pacing rate indicator can be a signed adjustment value or code that specifies how much the LP should increase its pacing rate (if the signed adjustment value or code has a positive sign) or decrease its pacing rate (if the signed adjustment value or code has a negative sign). Where an LP is to adjust its pacing rate to be equal to a new rate indicated by another LP or other type of IMD, rather than jump right to the new rate, the LP may gradually adjust its pacing rate, e.g., linearly, exponentially, or in some other manner.

If the answer the determination at step 606 is No (meaning that the received i2i message does not include a pacing rate indicator), then flow goes to step 610 and there is no adjustment to the pacing rate. If the answer the determination at step 606 is Yes (meaning that the received i2i message does include a pacing rate indicator), then flow goes to step 608 and there is a determination as to whether adjusting the pacing rate to match the rate specified by the pacing rate indicator would cause an adjustment to the pacing rate to exceed a rate adjustment threshold. The rate adjustment threshold can be a predetermined value (e.g., 15 bpm, or 20 bpm). Alternatively, the rate adjustment threshold can be a predetermined function of the present pacing rate. For example, the rate adjustment threshold can be a predetermined percentage (e.g., 15% or 20%) of the present pacing rate. For another example, the rate adjustment threshold can be a predetermined percentage (e.g., 25%) of a difference between the present pacing rate (e.g., 80 bpm) and a base pacing rate (e.g., 60 bpm). For a further example, the rate adjustment threshold can be limited to the greater of (or the lesser of) a predetermined value, a predetermine percentage of the present pacing rate, or a predetermined percentage of a difference between the present pacing rate and a base pacing rate. Other variations are also possible and within the scope of the embodiments described herein. Further, it is noted that a rate adjustment threshold that is used when a pacing rate is being increased can differ from a rate adjustment threshold that is used when a pacing rate is being decreased. In other words, there can be a rate increase threshold and a rate decrease threshold, which may differ from one another.

If the answer the determination at step 608 is No (meaning that adjusting the pacing rate to match the rate specified by the pacing rate indicator would not cause the adjustment to the pacing rate to exceed the rate adjustment threshold), then flow goes to step 612. At step 612 an adjustment to the pacing rate is made to match the rate specified by the pacing rate indicator).

If the answer the determination at step 608 is Yes (meaning that adjusting the pacing rate to match the rate specified by the pacing rate indicator would cause the adjustment to the pacing rate to exceed the rate adjustment threshold), then flow goes to step 614. At step 614 the pacing rate is adjusted, but the amount by which the pacing rate is adjusted is limited to a specified amount. The specified amount (which the pacing rate adjustment is limited to) can be a predetermined value (e.g., 15 bpm or 20 bpm), or a predetermined function of the present pacing rate, but is not limited thereto. For example, the predetermined amount can be a predetermined percentage (e.g., 15% or 20%) of the present pacing rate. For another example, the predetermined amount can be a predetermined percentage (e.g., 25%) of a difference between the present pacing rate (e.g., 80 bpm) and a base pacing rate (e.g., 60 bpm). Other variations are also possible and within the scope of the embodiments described herein.

Periodic Reduction in Pacing Rate

Assume the vLP acts as a "master" and the aLP acts as a "slave" in a master/slave leadless pacemaker system configuration. As noted above, "lock-up" may occur, for example, if the aLP receives a false message that instructs the aLP to pace at a high rate, when the vLP is actually pacing at a low rate, thereby causing aLP to pace the atrium at a much higher rate than the vLP is pacing the ventricle. To avoid the aLP from remaining out of sync with the vLP indefinitely, whenever the aLP does not receive an i2i message from the vLP for at least a specified period, the aLP will periodically (e.g., once per specified length of time, or once per specified number of cardiac cycles) reduce its pacing rate by a specified amount (e.g., value or percentage), thereby eventually causing the pacing rate aLP to get close enough to the pacing rate of the vLP such that the aLP can receive i2i messaged from the vLP and the aLP and the vLP can get back in sync with one another. Such embodiments can also be used where one or more LPs are configured to adjust their pacing rate in response to i2i messages including pacing rate indicators transmitted by another type of IMD, such as an S-ICD, but not limited thereto. More generally, such embodiments, which are described in additional detail below with reference to the high level flow diagram of FIG. 6B, are for use by a leadless pacemaker (LP) implanted in or on a first cardiac chamber of a patient that also has an implantable medical device (IMD) remotely located relative to the LP, wherein the LP is configured to pace the first cardiac chamber (e.g., the right atrial chamber, or the right ventricular chamber) and adjust a pacing rate at which the first cardiac chamber is paced based on a pacing rate indicator included in an i2i message received from the IMD (e.g., another LP, or an S-ICD).

Figure 6B:
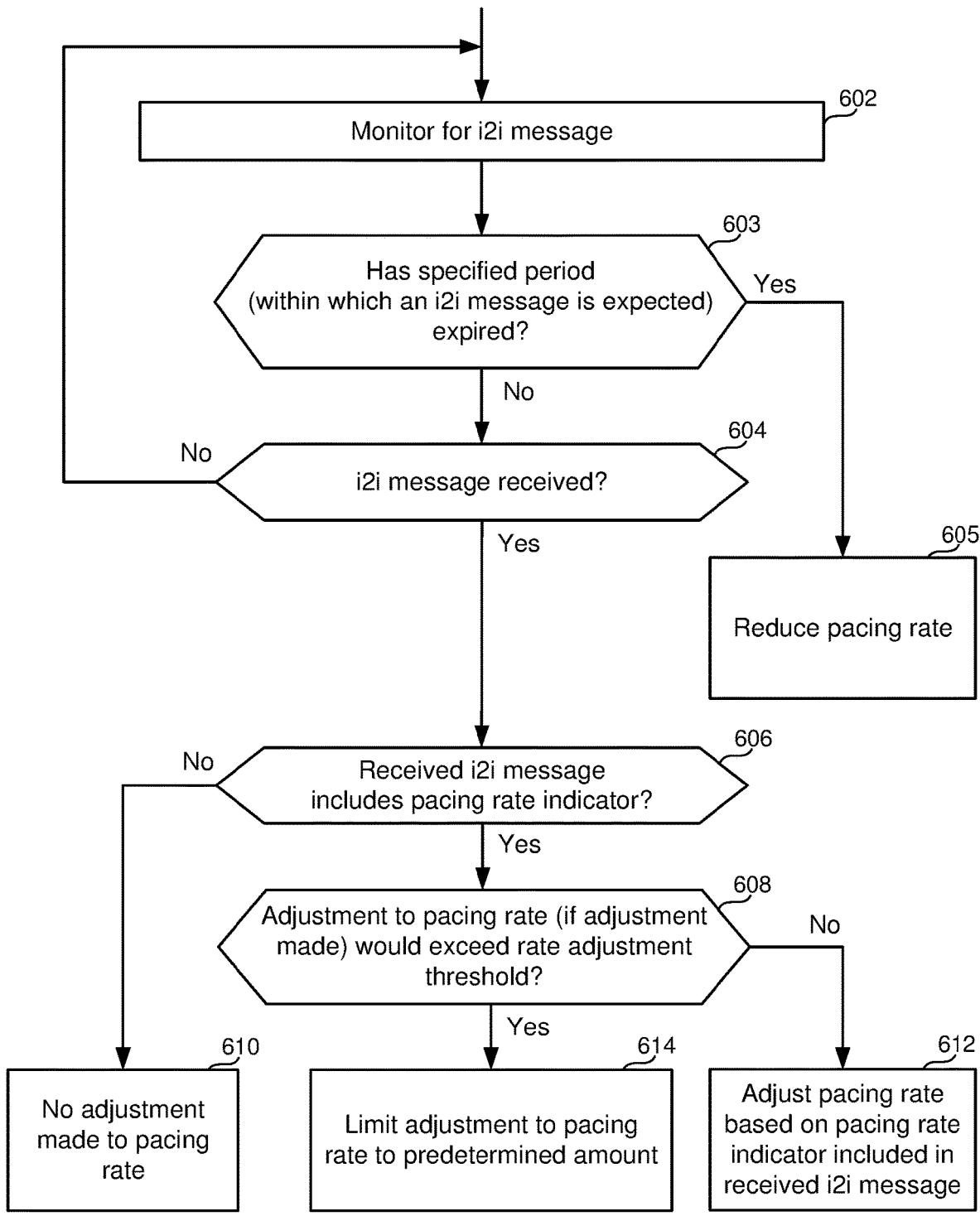
FIG. 6B is a high level flow diagram that is used to summarize methods for providing selective reductions in pacing rate, according to certain embodiments of the present technology.

Referring to FIG. 6B, step 602 involves the LP monitoring for i2i messages. Step 602 in FIG. 6B is the same as step 602 described above with reference to FIG. 6A, and thus, need not be described again. At step 603 there is a determination of whether a specified period (within which an i2i message that includes a pacing rate indicator is expected to be received, or within which specified a number of i2i message that include a pacing rate indicator is expected to be received) has expired. The specified period, which can also be referred to as an expected period, can be a predetermined period of time, e.g., 1 second, 1.5 seconds, 2 seconds, 5 seconds, or 10 seconds, but is not limited thereto. The expected period (aka specified period) can alternatively be a specified number (N) of cardiac cycles, where N is a predetermined integer that is equal to or greater than 1. For example, N can be 1, 2, 3, 5, 10, or 15, but is not limited thereto.

If the answer to the determination at step 603 is No, then flow goes to step 604. At step 604 there is a determination of whether an i2i message is received. If an i2i message is determined to have not been received, then flow returns to step 602 and the LP continues to monitor for an i2i message. If an i2i message is determined to have been received, then flow goes to step 606. Steps 604 and 606 are the same as steps 604 and 606 described above with reference to FIG. 6A, and thus, need not be described again. Additionally, steps 606, 608, 610, 612, and 614 in FIG. 6B are the same as those commonly numbered steps described above with reference 6A, and thus, need to be described again. In an alternative embodiment, the order of steps 603 and 604 are reversed, flow would go from step 604 to 603 if the answer to the determination at step 604 was No, flow would go from step 603 back to step 602 if the answer to step 603 was No, if the answer to step 603 was Yes flow would still go to step 605, and if the answer to step 604 was Yes flow would still go to step 606. In FIG. 6B, it would also be possible for flow to jump directly from step 606 to 612 in FIG. 6B, if the answer to the determination at step 606 is Yes. Other variations are also possible.

Returning to step 603 in FIG. 6B, if the answer to the determination at step 603 is Yes (meaning that a specified period within which an i2i message is expected to have been received has expired), then flow goes to step 605. At step 605, in response to the LP not receiving an i2i message within the expected period, the LP reduces its pacing rate at which it paces the cardiac chamber (e.g., a first cardiac chamber) it is responsible for pacing. At step 605 the amount by which the LP reduces the pacing rate at which the LP paces the first cardiac chamber, in response to the LP not receiving an i2i message within an expected period, can be a predetermined value, e.g., 5 bpm, 10 bpm, or 15 bpm, but is not limited thereto. Alternatively, at step 605 the amount by which the LP reduces the pacing rate can be a predetermined function of a present pacing rate. For example, the amount can be a predetermined percentage (e.g., 15% or 20%) of the present pacing rate. For another example, the amount can be a predetermined percentage (e.g., 25%) of a difference between the present pacing rate (e.g., 80 bpm) and a base pacing rate (e.g., 60 bpm). Other variations are also possible and within the scope of the embodiments described herein.

Multiple Messages

In accordance with certain embodiments of the present technology, when a second LP (or other type of IMD, e.g., an S-ICD) sends certain types of extended i2i messages to a first LP, the second LP (or other type of IMD) must send the extended i2i message at least M times (where M is an integer that is greater than or equal to 2) within a specified amount of time or cardiac cycles, and the first LP must receive the extended i2i message at least N times (where N is an integer that is greater than or equal to 2, and can be equal to or less than M) within the specified amount of time or cardiac cycles, in order for the first LP to follow instructions included in the extended i2i message. Exemplary types of extended i2i messages that a sending LP (or other type of IMD) must send at least M times, and the receiving LP must receive at least N times, can include, but are not limited to, an extended i2i message that includes at least one of a pacing rate indicator, a recommended replacement time (RRT) indicator, or an automatic mode switch (AMS) entry indicator, an AMS exit indicator, a magnet entry indicator, or a magnet exit indicator, but is not limited thereto.

Figure 6C:
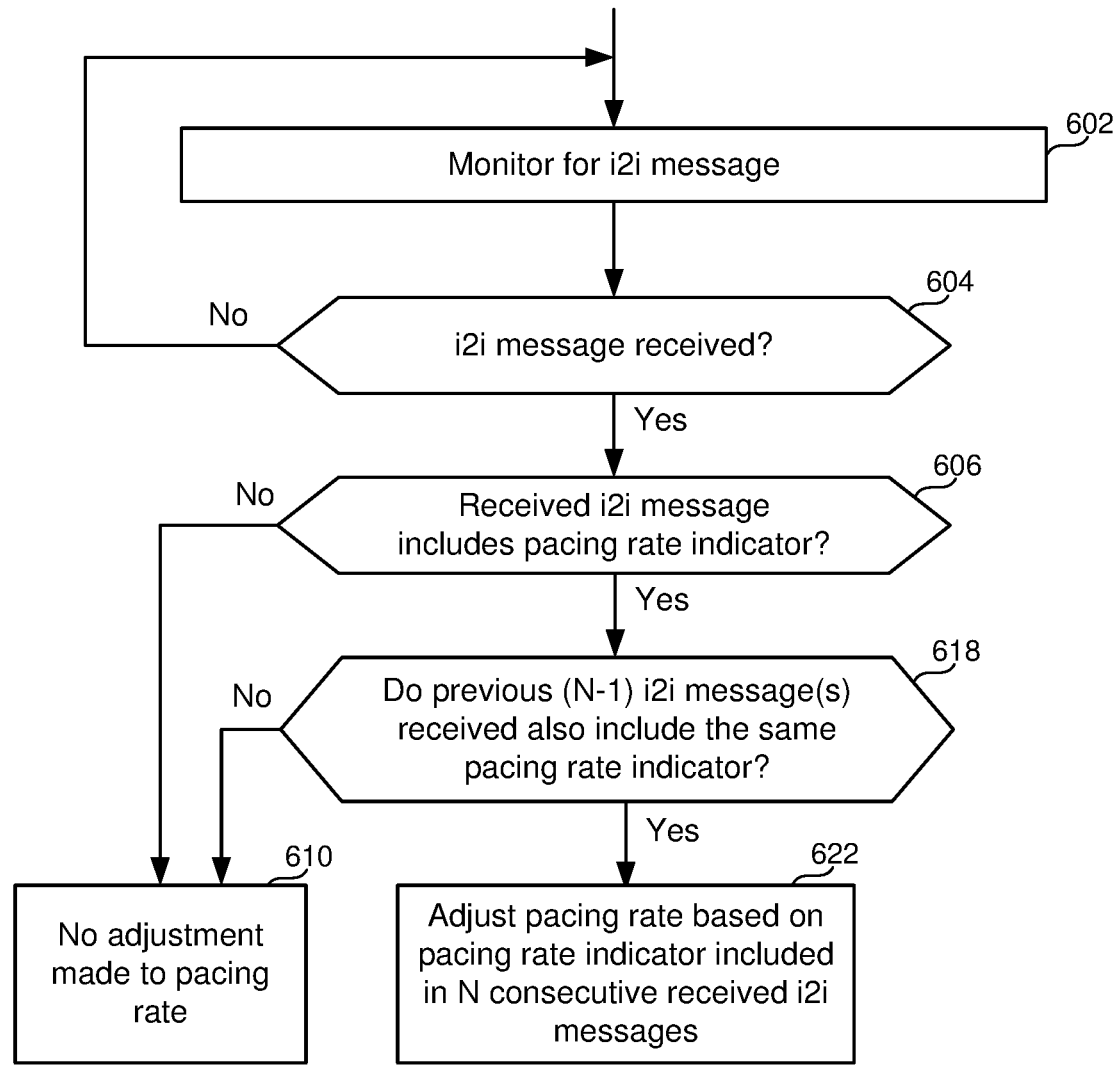
FIG. 6C is a high level flow diagram that is used to summarize methods in which multiple i2i messages must be sent to and received by an LP before the LP adjusts its pacing rate in response to receiving i2i messages including a pacing rate indicator, according to certain embodiments of the present technology.

The high level flow diagram of FIG. 6C will now be used to summarize methods in which multiple i2i messages including a pacing rate indicator must be sent to and received by an LP before the LP adjusts its pacing rate in response to receiving i2i messages including the pacing rate indicator. Such methods are for use by an LP implanted in or on a first cardiac chamber of a patient that also has an IMD remotely located relative to the LP, wherein the LP is configured to pace the first cardiac chamber and adjust a pacing rate at which the first cardiac chamber is paced based on a pacing rate indicator included in an i2i message received from the IMD. The IMD can be another LP implanted in or on a second cardiac chamber, or an S-ICD, but is not limited thereto. While FIG. 6C is described from the perspective of the LP that receives i2i messages (including pacing rate indicators) from another IMD (e.g., another LP), it should be understood that the IMD (e.g., another LP) that transmits the i2i messages (including pacing rate indicators) should be configured to transmit at least M consecutive i2i messages that include a pacing rate indicator whenever the IMD wants to cause the LP (to which the i2i messages are being sent) to change its pacing rate.

Referring to FIG. 6C, step 602 involves an LP monitoring for i2i messages, step 604 involves determining whether an i2i message was received, and step 606 involves determining whether a received i2i message includes a pacing rate indicator. Steps 602, 604, and 606 are the same as the commonly numbered steps described above with reference to FIG. 6A, and thus, need not be described again.

If the answer the determination at step 606 is No (meaning that the received i2i message does not include a pacing rate indicator), then flow goes to step 610 and there is no adjustment to the pacing rate. If the answer the determination at step 606 is Yes (meaning that the received i2i message does include a pacing rate indicator), then flow goes to step 618. At step 618 there is a determination of whether the previous N−1 i2i messages received also included the same pacing rate indicator. More generally, at step 602, 604, 606, and 618 there is a determination of whether N consecutive received i2i messages include the same pacing rate indicator, where N is an integer that is equal to or greater than 2. If the answer to the determination at step 618 is No, then flow goes to step 610 and there is no adjustment to the pacing rate. If the answer the determination at step 618 is Yes (meaning that N consecutive received i2i messages included the same pacing rate indicator), then flow goes to step 622. At step 622 the pacing rate is adjusted to based on the pacing rate indicator included in the N consecutive received i2i messages.

As noted above, a pacing rate indicator can, e.g., be a value indicating a pacing rate value (e.g., 80 bpm), a code that the LP that can look up (e.g., in a stored look up table) and corresponds to a pacing rate value, or a value that the LP feeds into an equation to determine the pacing rate, but is not limited thereto. Alternatively, the pacing rate indicator can be beat-to-beat interval value (e.g., 0.75 seconds), a code that the LP can look up and corresponds to a beat-to-beat interval value, or a value that the LP feeds into an equation to determine the beat-to-beat interval, but is not limited thereto. Other variations are also possible and within the scope of the embodiments described herein.

With respect to the embodiments described with reference to FIG. 6C, by requiring that an LP receive N consecutive i2i messages including the same pacing rate indicator, in order for the LP to change its pacing rate based on the pacing rate indicator, the probability that an LP adjusts its pacing rate in response to a false message is significantly reduced, which also has the effect of significantly reducing the probability one or more false messages will cause the above described lock-up problem. In other words, such embodiments take advantage of there being a very low probability that an LP receives multiple consecutive false i2i messages including a same pacing rate indicator. In certain alternative embodiments, rather than requiring that N consecutive i2i messages include the same pacing rate indicator, in order for an LP to change its pacing rate based on the pacing rate indicator, the LP can change its pacing rate so long as M out of N received i2i messages include the same pacing rate indicator, wherein M is a first specified integer that is 2 or greater, and N is a second specified integer that is greater than M (e.g., M=3 and N=5).

Selective Increased Error Detection and Correction Code Length

An LP may use cyclic redundancy check (CRC) or some other type of error detection and correction scheme to determine whether a message the LP receives is a valid message or an invalid message. The shorter a message is, the greater the probability that an LP may receive a "false message". Conversely, the longer a message is, the lower the probability that an LP may receive a "false message". However, using longer messages consumes more power than using shorter messages, and thus, it would not be practical from a device longevity standpoint for every message sent between LPs and/or other types of IMDs to be long messages.

Within an error detection and correction scheme, error detection generally refers to the detection of errors caused by noise or other impairments during transmission from a transmitter of one device to a receiver of another device. Error correction generally refers to the detection of errors and reconstruction of the original, error-free data, if possible. Typically, to enable error detection and correction to be performed, some redundancy (i.e., some extra data) is added to a message, which enables a receiver to check consistency of the received message, and to recover data determined to be corrupted. Error detection is often realized using a suitable hash function (or checksum algorithm) that adds a fixed-length tag to a message, which enables receivers to verify the delivered message by recomputing the tag and comparing it with the one provided. For example, a repetition code can be used, where a repetition code is a coding scheme that repeats the bits across a channel to attempt to achieve error-free communication. Such a repetition code is often inefficient, and can be susceptible to problems if the error occurs in exactly the same place for each group. However, an advantage of repetition codes is that they are extremely simple, and thus, are typically power efficient compared to more complex schemes. Instead of, or in addition to a repetition code, parity bits can be used, wherein a parity bit is a bit that is added to a group of source bits to ensure that a number of set bits (e.g., bits with value 1) in the outcome is even or odd. Alternatively, or additionally, checksums and/or cyclic redundancy checks can be utilized. A checksum of a message is a modular arithmetic sum of message code words of a fixed word length (e.g., byte values). The sum may be negated by means of a ones'-complement operation prior to transmission to detect errors resulting in all-zero messages. Checksum schemes can include parity bits, check digits, and longitudinal redundancy checks. A cyclic redundancy check (CRC) is a non-secure hash function designed to detect accidental changes to digital data.

Where an error is detected in a received message, such an error may often be corrected. Such error correction may involve the use of an automatic repeat request, an error-correcting code or a hybrid scheme, but is not limited thereto. Automatic repeat request (ARQ) is an error control technique for data transmission that makes use of error-detection codes, acknowledgment and/or negative acknowledgment messages, and timeouts to achieve reliable data transmission. An acknowledgment is a message sent by the receiver to indicate that it has correctly received a data frame. Usually, when a transmitter does not receive the acknowledgment before the timeout occurs (e.g., within a reasonable amount of time after sending the data frame), it retransmits the frame until it is either correctly received or the error persists beyond a predetermined number of retransmissions. An error-correcting code (ECC) or forward error correction (FEC) code is a process of adding redundant data, or parity data, to a message, such that it can be recovered by a receiver even when a number of errors (up to the capability of the code being used) were introduced, either during the process of transmission, or on storage. Since the receiver does not have to ask the sender for retransmission of the data, a backchannel is not required in forward error correction, and it is therefore suitable for simplex communication such as broadcasting. Hybrid ARQ is a combination of ARQ and forward error correction. The above description has been included to provide a high level of possible error correction and detection schemes, and is not intended to be limiting and/or all encompassing, as the embodiments of the present technology can be used with almost any already developed or future developed error correction and detection schemes.

While there exist other types of error detection and correction schemes besides CRC schemes, for much of the discussion herein it is assumed that a CRC scheme is used. Nevertheless, it should be clear the embodiments of the present technology can be used with other types of error detection and correction schemes besides CRC. When using a CRC scheme, the CRC is computed from a received message. The received message plus the CRC must match in order for the combined message to be considered valid. The more bits used for the CRC the less likely random noise will create a pattern that is coincidentally a message with a matching CRC. It's like adding more digits to a combination lock. By increasing the message length of certain types of messages, the probability of an LP receiving a "false message" that is one of those certain types of messages (e.g., a message including a pacing rate indicator, or a message including a critical message, but not limited thereto) is significantly reduced. By limiting the use of the longer messages to just certain types of messages, the increase in power consumption that coincides with using longer messages is limited. Exemplary types of messages with which this solution can be used include messages that include a pacing rate indicator, a recommended replacement time (RRT) indicator, an automatic mode switch (AMS) entry or exit indicator, or a magnet entry or exit indicator, and/or the like.

Figure 6D:
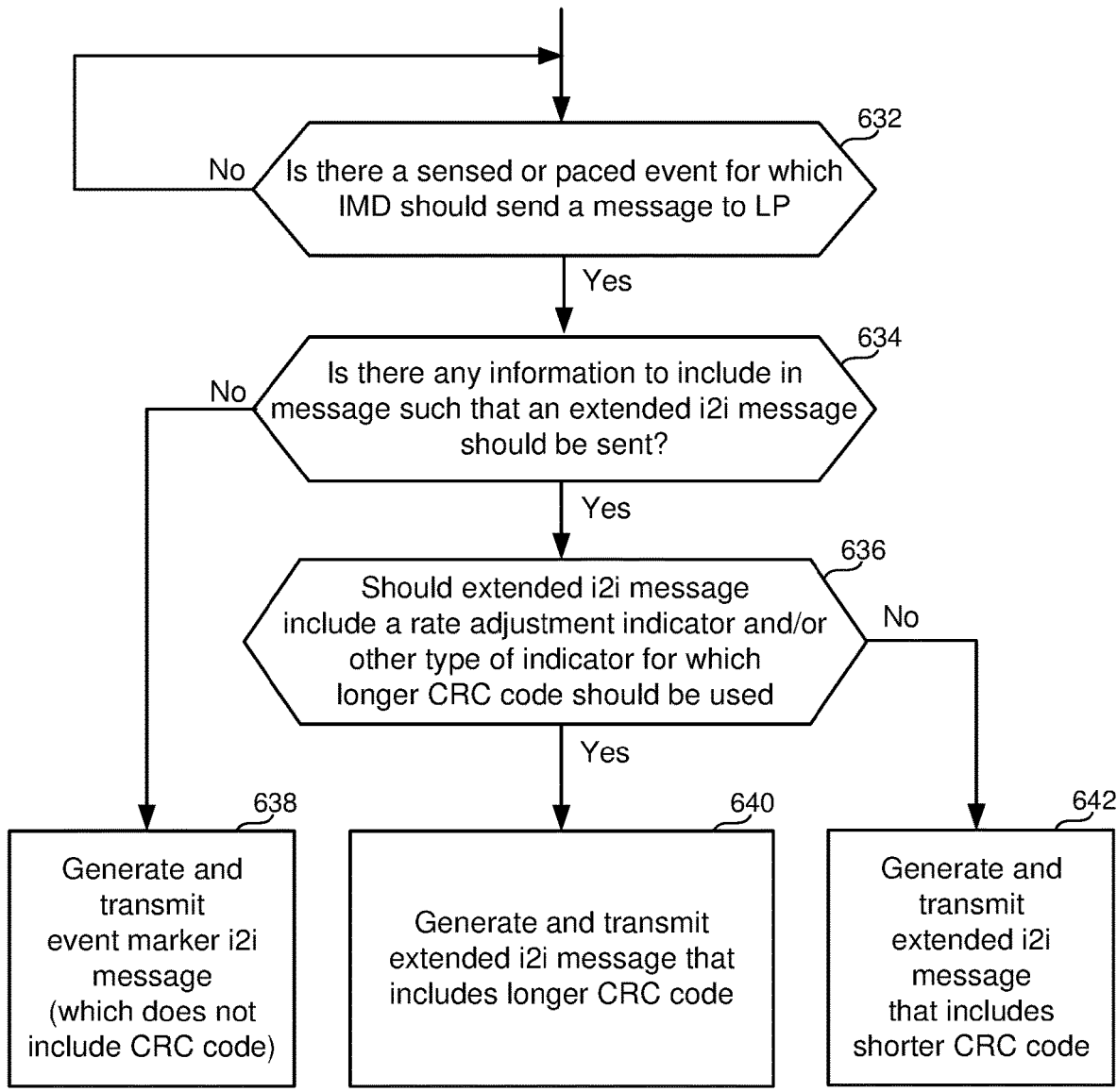
FIG. 6D is a high level flow diagram that is used to summarize methods in which i2i messages that include a pacing rate indicator include longer error detection and correction codes than certain other types of messages, according to certain embodiments of the present technology.

The high level flow diagram of FIG. 6D will now be used to summarize certain methods for use by an implantable system that includes an LP implanted in or on a first cardiac chamber of a patient and an IMD remotely located relative to the LP, wherein the LP is configured to pace the first cardiac chamber and adjust a pacing rate at which the first cardiac chamber is paced based on a pacing rate indicator included in an i2i message received from the IMD. The IMD can be another LP, or an ICD, such as an S-ICD, but is not limited thereto. Such embodiments are especially useful where an LP or an S-ICD is acting as a master device for an LP that is acting as a slave device. The flow diagram of FIG. 6D is described from the perspective of the IMD that is transmitting i2i messages to an LP that receives i2i messages and may adjust its pacing rate if a received i2i message includes a pacing rate indicator.

Referring to FIG. 6D, at step 632 an IMD determines whether there is an event (e.g., a sensed or paced event) or a trigger in response to which the IMD should send a message to a remotely located LP. For example, if the IMD is a vLP, the vLP may send an i2i message to a remotely located aLP whenever the vLP paces the right ventricle, or detects an intrinsic ventricular event. For another example, if the IMD is an S-ICD, in response to detecting a tachycardiac or some other event or condition, the S-ICD may send an i2i message to a vLP that instructs the vLP to deliver anti-tachycardia pacing (ATP). If the answer to step 632 is No, then step 632 is repeated until the answer to step 632 is Yes, at which point flow goes to step 634.

At step 634 the IMD (or more specifically, a controller thereof) determines whether there is information to include in the message such that an extended i2i message should be sent. If the answer to the determination at step 634 is No, then flow goes to step 638. At step 638 an event marker i2i message (which is not an extended message) is generated and transmitted.

If the answer to the determination at step 634 is Yes, then flow goes to step 636. At step 636 there is a determination of whether the extended i2i message should include a rate adjustment indicator and/or any other type of indicator (e.g., an RRT indicator, magnet entry indicator, magnet exit indicator, AMS entry indicator, AMS exit indicator, an ATP trigger, or a store EGM data trigger) for which a longer CRC code is to be used. The IMD may have a list or table of such message for which a longer CRC code should be used. If the answer to the determination at step 636 is No, then flow goes to step 642, where an extended i2i message including a shorter CRC code (e.g., a 4 bit CRC code) is generated and transmitted. If the answer to the determination at step 636 is Yes, then flow goes to step 640, where an extended i2i message including a longer CRC code (e.g., a 6 bit CRC code) is generated and transmitted. Other types of error correction and detection codes can alternatively be used in place of CRC codes.

The i2i messages transmitted at instances of steps 638, 640, and 642, or at least a subset of those instances, will be received by an LP to which the i2i messages are sent. The LP monitors for i2i messages, and in response to receiving an i2i message including a pacing rate indicator may adjust the rate at which the LP paces the cardiac chamber in (or on) which it is located. In such embodiments, i2i messages including pacing rate indicators that are transmitted from the IMD to the LP include longer error detection and correction codes compared to at least some of the i2i messages not including pacing rate indicators that are transmitted from the IMD to the LP. The use of longer error detection and correction codes (e.g., longer CRC codes) for certain types of messages reduces the probability that false messages for such types of messages will be received, which also has the effect of significantly reducing the probability the one or more false messages will cause the above described lock-up problem.

The embodiments described above with reference to FIGS. 6A, 6B, 6C, and 6C may be used alone or in combination with one another. For example, an embodiment described with reference to FIG. 6A can be used alone or with one or more of the embodiments described with reference to FIG. 6B, 6C, and/or 6D. For another example, an embodiment described with reference to FIG. 6B can be used alone or in with one or more of the embodiments described with reference to FIG. 6A, 6C, and/or 6D. For a further example, the embodiments described with reference to FIG. 6C can be used alone or in combination with one or more of the embodiments described with reference to FIG. 6A, 6B and/or 6D. For still another example, the embodiment described with reference to FIG. 6D can be used alone or in combination with one or more of the embodiment described with reference to FIG. 6A, 6B and/or 6C.

Figure 7:
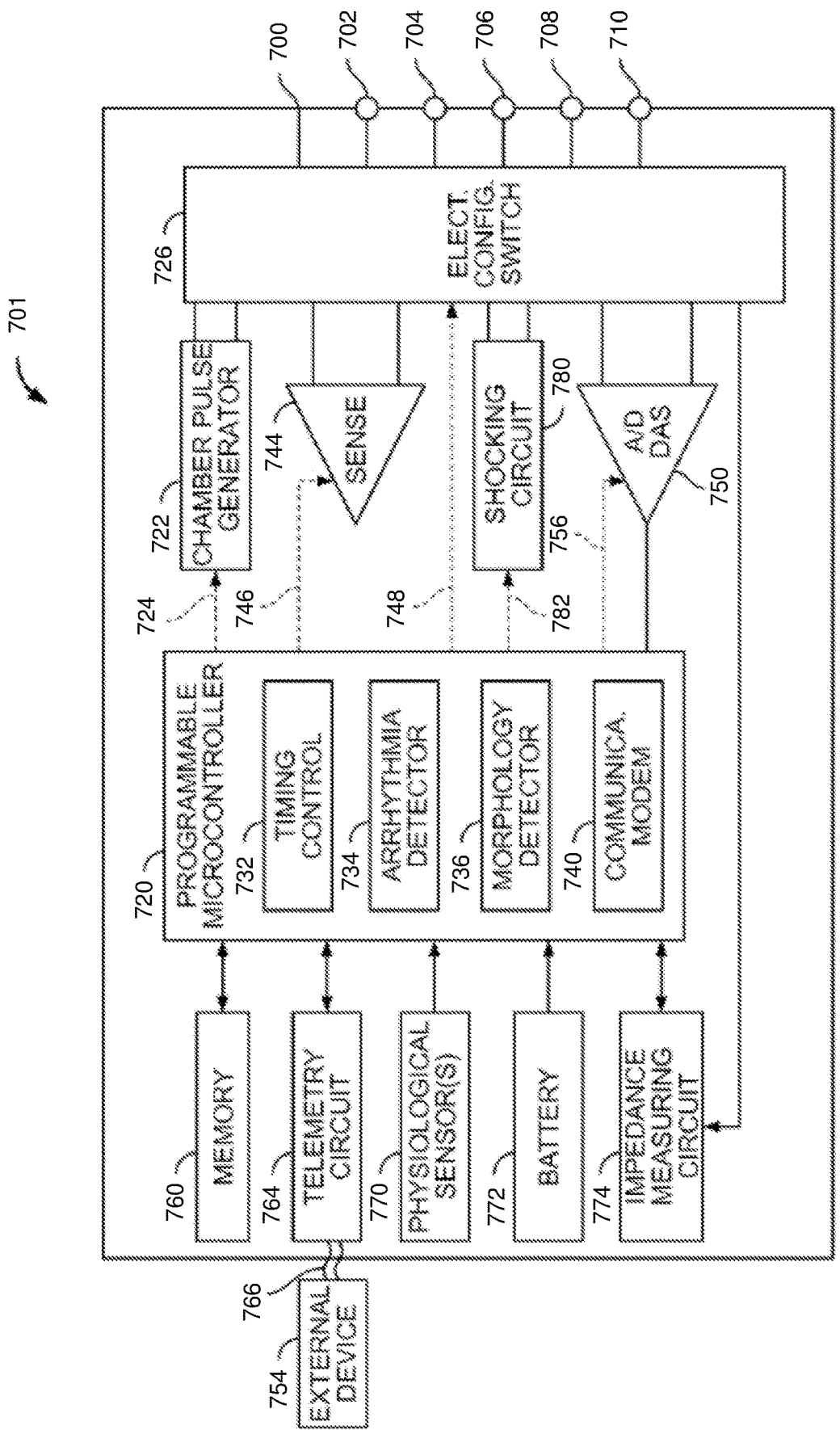
FIG. 7 shows a block diagram of one embodiment of an IMD (e.g., LP or in ICD) that is implanted into the patient as part of the implantable cardiac system in accordance with certain embodiments herein.

FIG. 7 shows a block diagram of one embodiment of an IMD (e.g., an LP or ICD) 701 that is implanted into the patient as part of the implantable cardiac system in accordance with certain embodiments herein. IMD 701 may be implemented as a full-function biventricular pacemaker, equipped with both atrial and ventricular sensing and pacing circuitry for four chamber sensing and stimulation therapy (including both pacing and shock treatment). Optionally, IMD 701 may provide full-function cardiac resynchronization therapy. Alternatively, IMD 701 may be implemented with a reduced set of functions and components. For instance, the IMD may be implemented without ventricular sensing and pacing.

IMD 701 has a housing 700 to hold the electronic/computing components. Housing 700 (which is often referred to as the "can", "case", "encasing", or "case electrode") may be programmably selected to act as the return electrode for certain stimulus modes. Housing 700 may further include a connector (not shown) with a plurality of terminals 702, 704, 706, 708, and 710. The terminals may be connected to electrodes that are located in various locations on housing 700 or elsewhere within and about the heart. IMD 701 includes a programmable microcontroller 720 that controls various operations of IMD 701, including cardiac monitoring and stimulation therapy. Microcontroller 720 includes a microprocessor (or equivalent control circuitry), RAM and/or ROM memory, logic and timing circuitry, state machine circuitry, and I/O circuitry.

IMD 701 further includes a first pulse generator 722 that generates stimulation pulses for delivery by one or more electrodes coupled thereto. Pulse generator 722 is controlled by microcontroller 720 via control signal 724. Pulse generator 722 may be coupled to the select electrode(s) via an electrode configuration switch 726, which includes multiple switches for connecting the desired electrodes to the appropriate I/O circuits, thereby facilitating electrode programmability. Switch 726 is controlled by a control signal 728 from microcontroller 720.

In the embodiment of FIG. 7, a single pulse generator 722 is illustrated. Optionally, the IMD may include multiple pulse generators, similar to pulse generator 722, where each pulse generator is coupled to one or more electrodes and controlled by microcontroller 720 to deliver select stimulus pulse(s) to the corresponding one or more electrodes.

Microcontroller 720 is illustrated as including timing control circuitry 732 to control the timing of the stimulation pulses (e.g., pacing rate, atrio-ventricular (AV) delay, atrial interconduction (A-A) delay, or ventricular interconduction (V-V) delay, etc.). Timing control circuitry 732 may also be used for the timing of refractory periods, blanking intervals, noise detection windows, evoked response windows, alert intervals, marker channel timing, and so on. Microcontroller 720 also has an arrhythmia detector 734 for detecting arrhythmia conditions and a morphology detector 736. Although not shown, the microcontroller 720 may further include other dedicated circuitry and/or firmware/software components that assist in monitoring various conditions of the patient's heart and managing pacing therapies.

IMD 701 is further equipped with a communication modem (modulator/demodulator) 740 to enable wireless communication with the remote slave pacing unit. Modem 740 may include one or more transmitters and two or more receivers as discussed herein in connection with FIG. 2. In one implementation, modem 740 may use low or high frequency modulation. As one example, modem 740 may transmit i2i messages and other signals through conductive communication between a pair of electrodes. Modem 740 may be implemented in hardware as part of microcontroller 720, or as software/firmware instructions programmed into and executed by microcontroller 720. Alternatively, modem 740 may reside separately from the microcontroller as a standalone component.

IMD 701 includes a sensing circuit 744 selectively coupled to one or more electrodes, that perform sensing operations, through switch 726 to detect the presence of cardiac activity in the right chambers of the heart. Sensing circuit 744 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit to sense low amplitude signal characteristics of atrial fibrillation. Switch 726 determines the sensing polarity of the cardiac signal by selectively closing the appropriate switches. In this way, the clinician may program the sensing polarity independent of the stimulation polarity.

The output of sensing circuit 744 is connected to microcontroller 720 which, in turn, triggers or inhibits the pulse generator 722 in response to the presence or absence of cardiac activity. Sensing circuit 744 receives a control signal 746 from microcontroller 720 for purposes of controlling the gain, threshold, polarization charge removal circuitry (not shown), and the timing of any blocking circuitry (not shown) coupled to the inputs of the sensing circuitry.

In the embodiment of FIG. 7, a single sensing circuit 744 is illustrated. Optionally, the IMD may include multiple sensing circuits, similar to sensing circuit 744, where each sensing circuit is coupled to one or more electrodes and controlled by microcontroller 720 to sense electrical activity detected at the corresponding one or more electrodes. Sensing circuit 744 may operate in a unipolar sensing configuration or in a bipolar sensing configuration.

IMD 701 further includes an analog-to-digital (A/D) data acquisition system (DAS) 750 coupled to one or more electrodes via switch 726 to sample cardiac signals across any pair of desired electrodes. Data acquisition system 750 is configured to acquire intracardiac electrogram signals, convert the raw analog data into digital data, and store the digital data for later processing and/or telemetric transmission to an external device 754 (e.g., a programmer, local transceiver, or a diagnostic system analyzer). Data acquisition system 750 is controlled by a control signal 756 from the microcontroller 720.

Microcontroller 720 is coupled to a memory 760 by a suitable data/address bus. The programmable operating parameters used by microcontroller 720 are stored in memory 760 and used to customize the operation of IMD 701 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy.

The operating parameters of IMD 701 may be non-invasively programmed into memory 760 through a telemetry circuit 764 in telemetric communication via communication link 766 with external device 754. Telemetry circuit 764 allows intracardiac electrograms and status information relating to the operation of IMD 701 (as contained in microcontroller 720 or memory 760) to be sent to external device 754 through communication link 766.

IMD 701 can further include magnet detection circuitry (not shown), coupled to microcontroller 720, to detect when a magnet is placed over the unit. A magnet may be used by a clinician to perform various test functions of IMD 701 and/or to signal microcontroller 720 that external device 754 is in place to receive or transmit data to microcontroller 720 through telemetry circuits 764.

IMD 701 can further include one or more physiological sensors 770. Such sensors are commonly referred to as "rate-responsive" sensors because they are typically used to adjust pacing stimulation rates according to the exercise state of the patient. However, physiological sensor 770 may further be used to detect changes in cardiac output, changes in the physiological condition of the heart, or diurnal changes in activity (e.g., detecting sleep and wake states). Signals generated by physiological sensors 770 are passed to microcontroller 720 for analysis. Microcontroller 720 responds by adjusting the various pacing parameters (such as rate, AV Delay, V-V Delay, etc.) at which the atrial and ventricular pacing pulses are administered. While shown as being included within IMD 701, physiological sensor(s) 770 may be external to IMD 701, yet still be implanted within or carried by the patient. Examples of physiologic sensors might include sensors that, for example, sense respiration rate, pH of blood, ventricular gradient, activity, position/posture, minute ventilation (MV), and so forth.

A battery 772 provides operating power to all of the components in IMD 701. Battery 772 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). Battery 772 also desirably has a predictable discharge characteristic so that elective replacement time can be detected. As one example, IMD 701 employs lithium/silver vanadium oxide batteries.

IMD 701 further includes an impedance measuring circuit 774, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. Impedance measuring circuit 774 is coupled to switch 726 so that any desired electrode may be used. In this embodiment IMD 701 further includes a shocking circuit 780 coupled to microcontroller 720 by a data/address bus 782.

In some embodiments, the LPs 102a and 102b are configured to be implantable in any chamber of the heart, namely either atrium (RA, LA) or either ventricle (RV, LV). Furthermore, for dual-chamber configurations, multiple LPs may be co-implanted (e.g., one in the RA and one in the RV, one in the RV and one in the coronary sinus proximate the LV). Certain pacemaker parameters and functions depend on (or assume) knowledge of the chamber in which the pacemaker is implanted (and thus with which the LP is interacting; e.g., pacing and/or sensing). Some non-limiting examples include sensing sensitivity, an evoked response algorithm, use of AF suppression in a local chamber, blanking & refractory periods, etc. Accordingly, each LP needs to know an identity of the chamber in which the LP is implanted, and processes may be implemented to automatically identify a local chamber associated with each LP.

Processes for chamber identification may also be applied to subcutaneous pacemakers, ICDs, with leads and the like. A device with one or more implanted leads, identification and/or confirmation of the chamber into which the lead was implanted could be useful in several pertinent scenarios. For example, for a DR or CRT device, automatic identification and confirmation could mitigate against the possibility of the clinician inadvertently placing the V lead into the A port of the implantable medical device, and vice-versa. As another example, for an SR device, automatic identification of implanted chamber could enable the device and/or programmer to select and present the proper subset of pacing modes (e.g., AAI or WI), and for the IPG to utilize the proper set of settings and algorithms (e.g., V-AutoCapture vs ACap-Confirm, sensing sensitivities, etc.).

While many of the embodiments of the present technology described above have been described as being for use with LP type IMDs, embodiments of the present technology that are for use in reducing how often a first receiver of an IMD wakes up a second receiver of an IMD, in order to reduce power consumption, can also be used with other types of IMDs besides an LP. Accordingly, unless specifically limited to use with an LP, the claims should not be limited to use with LP type IMDs.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments of the present technology without departing from its scope. While the dimensions, types of materials and coatings described herein are intended to define the parameters of the embodiments of the present technology, they are by no means limiting and are exemplary embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A method for use by a system including a leadless pacemaker (LP) implanted in or on a first cardiac chamber of a patient and an implantable medical device (IMD) remotely located relative to the LP, wherein the LP is configured to pace the first cardiac chamber based on implant-to-implant (i2i) messages received from the IMD and adjust a pacing rate at which the first cardiac chamber is paced based on pacing rate indicators included in some i2i messages received from the IMD, the method comprising:
the IMD transmitting i2i messages to the LP, wherein a first subset of the i2i messages are non-extended i2i messages used to only inform the LP of sensed or paced events, a second subset of the i2i messages are first extended i2i messages used to inform the LP of sensed or paced events as well as one or more first types of indicators, and a third subset of the i2i messages are second extended i2i messages used to inform the LP of sensed or paced events as well as one or more second types of indicators that include pacing rate indicators; and
the LP monitoring for the i2i messages and pacing the first cardiac chamber based on the i2i messages received from the IMD, including adjusting the pacing rate at which the first cardiac chamber is paced based on at least some of the pacing rate indicators included in at least some of the i2i messages received by the LP from the IMD;
wherein the first subset of the i2i messages are devoid of error detection and correction codes, the second subset of the i2i messages include error detection and correction codes having a first length, and the third subset of the i2i messages including the pacing rate indicators include error detection and correction codes having a second length that is longer than the first length.

2. The method of claim 1, wherein the error detection and correction codes comprise cyclic redundancy check (CRC) codes.

3. The method of claim 1, wherein:
the LP comprises a first LP (LP1); and
the IMD comprises a second LP (LP2) implanted in or on a second cardiac chamber.

4. The method of claim 1, wherein the IMD comprises a subcutaneous implantable cardioverter defibrillator (S-ICD).

5. The method of claim 1, wherein the i2i messages are transmitted and received via conductive communication.

6. A system comprising:
a leadless pacemaker (LP) configured to be implanted in or on a first cardiac chamber of a patient and configured to pace the first cardiac chamber; and
an implantable medical device (IMD) remotely located relative to the LP;
the LP configured to monitor for implant-to-implant (i2i) messages and adjust a pacing rate at which the first cardiac chamber is paced based on pacing rate indicators included in some of the i2i messages received from the IMD;
the IMD configured to transmit i2i messages to the LP, wherein a first subset of the i2i messages are non-extended i2i messages used to only inform the LP of sensed or paced events, a second subset of the i2i messages are first extended i2i messages used to inform the LP of sensed or paced events as well as one or more first types of indicators, and a third subset of the i2i messages are second extended i2i messages used to inform the LP of sensed or paced events as well as one or more second types of indicators that include pacing rate indicators; and
the IMD configured to include no error detection and correction codes in the first subset of the i2i messages, include error detection and correction codes having a first length in the second subset of i2i messages, and include error detection and correction codes having a second length that is greater than the first length in the third subset of i2i messages.

7. The system of claim 6, wherein the error detection and correction codes comprise cyclic redundancy check (CRC) codes.

8. The system of claim 6, wherein:
the LP comprises a first LP (LP1); and
the IMD comprises a second LP (LP2) implanted in or on a second cardiac chamber.

9. The system of claim 6, wherein the IMD comprises a subcutaneous implantable cardioverter defibrillator (S-ICD).

10. The system of claim 6, wherein the i2i messages are transmitted and received via conductive communication.

* * * * *